(12) United States Patent
Miller et al.

(10) Patent No.: US 10,265,301 B2
(45) Date of Patent: Apr. 23, 2019

(54) FORMULATIONS OF DEFERASIROX AND METHODS OF MAKING THE SAME

(71) Applicant: DISPERSOL TECHNOLOGIES, LLC, Georgetown, TX (US)

(72) Inventors: Dave A. Miller, Round Rock, TX (US); Justin M. Keen, Round Rock, TX (US); Sandra U. Kucera, Cedar Park, TX (US)

(73) Assignee: DISPERSOL TECHNOLOGIES, LLC, Georgetown, TX (US)

( * ) Notice: Subject to any disclaimer, the term of this patent is extended or adjusted under 35 U.S.C. 154(b) by 0 days.

(21) Appl. No.: 15/185,888

(22) Filed: Jun. 17, 2016

(65) Prior Publication Data

US 2017/0027911 A1   Feb. 2, 2017

Related U.S. Application Data

(60) Provisional application No. 62/180,998, filed on Jun. 17, 2015.

(51) Int. Cl.
| | | |
|---|---|---|
| A61K 31/4196 | (2006.01) | |
| A61K 9/14 | (2006.01) | |
| A61K 9/20 | (2006.01) | |
| A61P 39/04 | (2006.01) | |

(52) U.S. Cl.
CPC .......... *A61K 31/4196* (2013.01); *A61K 9/146* (2013.01); *A61K 9/2054* (2013.01); *A61P 39/04* (2018.01)

(58) Field of Classification Search
CPC ........ A61K 9/146; A61K 9/31; A61K 9/4196; A61K 9/2054
See application file for complete search history.

(56) References Cited

U.S. PATENT DOCUMENTS

| | | | | |
|---|---|---|---|---|
| 2008/0311194 A1* | 12/2008 | Battung | ............... | A61K 9/0095 424/465 |
| 2009/0142395 A1* | 6/2009 | Zadok | .................. | A61K 9/0095 424/465 |
| 2012/0245361 A1* | 9/2012 | Mizhiritskii | ......... | C07D 291/06 548/110 |
| 2013/0142871 A1 | 6/2013 | Paetz et al. | | |
| 2014/0147503 A1 | 5/2014 | Malhotra et al. | | |
| 2015/0017241 A1 | 1/2015 | Ghosh et al. | | |
| 2016/0120847 A1 | 5/2016 | Malhotra et al. | | |

FOREIGN PATENT DOCUMENTS

WO    WO 2014/181108    11/2014

OTHER PUBLICATIONS

Bennett, et al., "Preparation of amorphous solid dispersions by rotary evaporation and KineticSol Dispersing: approaches to enhance solubility of a poorly water-soluble gum extract," *Drug Dev. Ind. Pharm.*, 41:382-97, 2015.
Chirnomas, et al., "Deferasirox pharmacokinetics in patients with adequate versus inadequate response," *Blood*, 114:4009-13, 2009.
DiNunzio, et al al., "Production of advanced solid dispersions for enhanced bioavailability of itraconazole using KinetiSol Dispersig," *Drug Dev. Ind. Pharm.*, 36:1064-78, 2010.
Fan, et al., "Impact of polymers on dissolution performance of an amorphous gelleable drug from surface-coated beads," *Eur. J. Pharm. Sci.*, 37:1-10, 2009.
Hughey, et al., "Dissolution enhancement of a drug exhibiting thermal and acidic decomposition characteristics by fusion processing: a comparative study of hot melt extrusion and KinetiSol dispersing," *AAPS PharmSciTech*, 11:760-74, 2010.
Hughey, et al., "Thermal processing of poorly water-soluble drug substance exhibiting a high melting point: the utility of KinetiSol® Dispersing," *Int. J. Pharm.*, 419:222-30, 2011.
Invitation to Pay Additional Fees issued in International Application Serial No. PCT/US2016/038089, dated Aug. 22, 2016.
International Search Report and Written Opinion ssued in International Application Serial No. PCT/US2016/038089, dated Oct. 24, 2016.
Miller et al., "Targeted intestinal delivery of supersaturated itraconazole for improved oral absorption," *Pharm. Res.*, 25:1450-9, 2008.
Miller, et al., "Enhanced in vivo absorption of itraconazole via stabilization of supersaturation following acidic-to-neutral pH transition," *Drug Dev. Ind. Pharm.*, 34:890-902, 2008.
Nick, et al., "ICL670A: preclinical profile," *Adv. Exp. Med. Biol.*, 509:185-203, 2002.
Waldmeier, et al., "Pharmacokinetics, metabolism, and dispositions of deferasirox in beta-thalassemic patients with transfusion-dependent iron overload who are at pharmacokinetic steady state," *Drug Metab. Dispos.*, 38:808-16, 2010.
Chang, et al.., "Improved efficacy and tolerability of oral deferasirox by twice-daily dosing for patients with transfusion-dependent β-Thalassemia," *Pediatr. Blood Cancer*, 56:420-424, 2011.
Hughey, et al., "Dissolution enhancement of a drug exhibiting thermal and acidic decomposition characteristics by fusion processing: a comparative study of hot melt extrusion and KinetiSol® dispersing," *AAPS PharmaSciTech*, 11:760-74, 2010.

(Continued)

*Primary Examiner* — Johann R Richter
*Assistant Examiner* — Genevieve S Alley
(74) *Attorney, Agent, or Firm* — Parker Highlander PLLC

(57) ABSTRACT

The disclosure provides for improved pharmaceutical compositions containing deferasirox (DFX) and methods of manufacturing the same. In particular, the compositions are prepared using thermokinetic compounding and provide improved properties as well as more efficient methods of manufacture.

24 Claims, 19 Drawing Sheets
(19 of 19 Drawing Sheet(s) Filed in Color)

(56) References Cited

OTHER PUBLICATIONS

Extended European Search Report issued in corresponding European Application No. 16812529.2, dated Nov. 9, 2018.
Van den Mooter, "The use of amorphous solid dispersions: A formulation strategy to overcome poor solubility and dissolution rate", *Drug Discov. Today Technol.*, 9(2):e79-e85, 2012.

* cited by examiner

FORMULATIONS OF DEFERASIROX AND METHODS OF MAKING THE SAME

This application claims benefit of priority to U.S. Provisional Application Ser. No. 62/180,998, filed Jun. 17, 2015, the entire contents of which are hereby incorporated by reference.

BACKGROUND

1. Field

The present disclosure relates in general to the field of pharmaceutical preparation and manufacturing, and more particularly, pharmaceutical formulations of deferasirox using thermokinetic compounding.

2. Description of Related Art

The beneficial applications of many potentially therapeutic molecules is often not fully realized either because they are abandoned during development due to poor pharmacokinetic profiles, or because of suboptimal product performance. Alternatively, even if produced, the cost associated with formulating such molecules may create barriers to their widespread use. Problems with formulation are often due to poor solubility, resulting in poor bioavailability, increased expense, and ultimately termination of the product. In recent years, the pharmaceutical industry has begun to rely more heavily on formulational methods for improving drug solubility. Consequently, advanced formulation technologies aimed at enhancing the dissolution properties of poorly water soluble drugs are becoming increasingly important to modern drug delivery.

Deferasirox (DFX; marketed as Exjade®, Desirox®, Defrijet®, Desifer®, Jadenu®) is an oral iron chelator. Its main use is to reduce chronic iron overload in patients who are receiving long-term blood transfusions for conditions such as β-thalassemia and other chronic anemias. It is the first oral medication approved in the USA for this purpose. It was approved by the United States Food and Drug Administration (FDA) in November, 2005. According to the FDA (May, 2007), renal failure and cytopenias have been reported in patients receiving deferasirox oral suspension tablets. It is approved in the European Union by the European Medicines Agency (EMA) for children 6 years and older for chronic iron overload from repeated blood transfusions.

The pharmacokinetics of orally administered DFX can be characterized as highly variable with the most probable source of variability being its pH-dependent solubility. Weakly acidic compounds with low solubility in gastric fluid have a tendency to form insoluble aggregated structures when exposed to acidic media for extended durations absent the proper delivery system. When these insoluble structures are formed in the stomach, dissolution and absorption of the compound from the intestinal lumen is substantially reduced despite relatively good solubility of the free compound in intestinal fluids. As gastrointestinal pH can vary widely for a given individual from day-to-day and between individuals based on nutritional and diseased states and/or the influence of medications, it is understood that the solubility properties of DFX can lead to erratic oral absorption, and consequently, diminished therapeutic outcomes.

Thus, while deferasirox has significant therapeutic value for chronic iron overload, it also exhibits extremely challenging properties with respect to pharmaceutical formulation. As a result, there is a great need in to provide improved compositions and methods of manufacturing for this drug.

SUMMARY

Thus, in accordance with the present disclosure, there is provided a method of making a pharmaceutical composition comprising (a) providing crystalline deferasirox (DFX) and one or more pharmaceutically acceptable excipients; (b) compounding the materials of step (a) in a thermokinetic mixer at less than or equal to 200° C. for less than about 300 seconds, wherein the thermokinetic compounding of DFX and the one or more pharmaceutically acceptable excipients forms a melt blended pharmaceutical composite. The pharmaceutical may comprise a second active pharmaceutical ingredient in addition to DFX, such as wherein the second active pharmaceutical ingredient is a second iron chelator, an agent used in the treatment or prevention of osteoporosis, an anti-fungal agent, or an agent that increases the rate of production of red blood cells, such as amphotericin B, deferiprone, deferoxamine, erythropoietin, or risedronate. Step (b) may comprise compounding the materials of step (a) in a thermokinetic mixer for less than about 240 seconds, less than about 180 seconds, less than about 120 second, less than about 90 seconds, less than about 60 seconds, or less than about 30 seconds.

The one or more pharmaceutically acceptable excipients may comprise a pharmaceutical polymer, a surfactant, or one or more surfactants and one or more polymer carriers. The composite may be an amorphous dispersion. The pharmaceutical polymer may comprise an agent selected from the group consisting of poly(vinyl acetate)-co-poly(vinylpyrrolidone) copolymer, ethylcellulose, hydroxypropylcellulose, cellulose acetate butyrate, poly(vinylpyrrolidone), poly(ethylene glycol), poly(ethylene oxide), poly(vinyl alcohol), hydroxypropyl methylcellulose, hydroxyethylcellulose, sodium carboxymethyl-cellulose, dimethylaminoethyl methacrylate-methacrylic acid ester copolymer, ethylacrylate-methylmethacrylate copolymer, cellulose acetate phthalate, cellulose acetate trimelletate, poly(vinyl acetate) phthalate, hydroxypropylmethylcellulose phthalate, poly (methacrylate ethylacrylate) (1:1) copolymer, poly (methacrylate methylmethacrylate) (1:1) copolymer, poly (methacrylate methylmethacrylate) (1:2) copolymer, hydroxypropylmethylcellulose acetate succinate and polyvinyl caprolactam-polyvinyl acetate-polyethylene glycol graft copolymer.

The one or more surfactants may comprise an agent selected from the group consisting of sodium dodecyl sulfate, dioctyl sodium sulphosuccinate, polyoxyethylene (20) sorbitan monooleate, glycerol polyethylene glycol oxystearate-fatty acid glycerol polyglycol esters-polyethylene glycols-glycerol ethoxylate, glycerol-polyethylene glycol ricinoleate-fatty acid esters of polyethyleneglycol-polyethylene glycols-ethoxylated glycerol, vitamin E TPGS and sorbitan laurate.

In particular cases, the surfactant comprises an agent selected from the group consisting of sodium dodecyl sulfate, dioctyl sodium sulphosuccinate, polyoxyethylene (20) sorbitan monooleate, glycerol polyethylene glycol oxystearate-fatty acid glycerol polyglycol esters-polyethylene glycols-glycerol ethoxylate, glycerol-polyethylene glycol ricinoleate-fatty acid esters of polyethyleneglycol-polyethylene glycols-ethoxylated glycerol, vitamin E TPGS, and sorbitan laurate, and the pharmaceutical polymer comprises an agent selected from a group consisting of poly(vinyl acetate)-co-poly(vinylpyrrolidone) copolymer, ethylcellulose, hydroxypropylcellulose, cellulose acetate butyrate, poly(vinylpyrrolidone), poly(ethylene glycol), poly(ethylene oxide), poly(vinyl alcohol), hydroxypropyl methylcellulose, hydroxyethylcellulose, sodium carboxymethyl-cellulose, dimethylaminoethyl methacrylate-methacrylic acid ester copolymer, ethylacrylate-methylmethacrylate copolymer, cellulose acetate phthalate, cellulose acetate trimelletate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropylmethylcellulose acetate succinate and polyvinyl caprolactam-polyvinyl acetate-polyethylene glycol graft copolymer.

The composition may remain amorphous per x-ray diffraction analysis following storage in an open container at about 40° C., relative humidity of about 75%, at five weeks. The composition may comprise about 30%-60% DFX, about 40%-60% DFX, about 30% DFX, 35% DFX, 40% DFX, 45% DFX, 50% DFX, 55% DFX, or 60% DFX. Step (b) may be performed at a temperature of about 100° C., about 125° C., about 150° C., about 180° C., or about 100° C. to 200° C. The composition may have a single glass transition temperature. The purity of DFX in said composition may be about 95%, is about 99%, is about 99.5%, or is about 95% to about 100%. The DFX to pharmaceutical polymer ratio may be about 2:8 to about 7:3, including about 3:7, about 4:6, about 1:1, or about 6:4.

The one or more pharmaceutically acceptable excipients may comprise a processing agent, such as a plasticizer. Alternatively, the composition may not contain a processing agent/plasticizer. The one or more pharmaceutically acceptable excipients comprises a water soluble pharmaceutical polymer, such as a water soluble polymer selected from a group consisting of poly(vinyl acetate)-co-poly(vinylpyrrolidone) copolymer, poly(vinylpyrrolidone), cellulose acetate phthalate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropyl methylcellulose, hydroxypropylmethylcellulose acetate succinate, poly(vinyl alcohol), and polyvinyl caprolactam-polyvinyl acetate-polyethylene glycol graft copolymer.

The one or more pharmaceutically acceptable excipients may comprise a cross-linked pharmaceutical polymer, such as carbomer, crospovidone, or croscarmellose sodium. The one or more pharmaceutically acceptable excipients may comprise a pharmaceutical polymer of high melt viscosity. The one or more pharmaceutically acceptable excipients may comprise a thermally labile pharmaceutical polymer. The one or more pharmaceutically acceptable excipients may comprise poly(methacrylate ethylacrylate) (1:1) copolymer or poly(vinyl acetate)-co-poly(vinylpyrrolidone). The one or more pharmaceutically acceptable excipients may comprise poly(methacrylate ethylacrylate) (1:1) copolymer and poly(vinyl acetate)-co-poly(vinylpyrrolidone). The one or more pharmaceutically acceptable excipients may comprise poly(vinyl acetate)-co-poly(vinylpyrrolidone) and hydroxypropylmethylcellulose acetate succinate.

In another embodiment, there is provided a pharmaceutical composition comprising an amorphous dispersion of deferasirox (DFX) and one or more pharmaceutically acceptable excipients. The composition may have a single glass transition temperature. The composition may remain amorphous per x-ray diffraction analysis following storage in an open container at about 40° C., relative humidity of about 75%, at five weeks. The one or more pharmaceutically acceptable excipients may comprise one or more polymers, a processing agent and/or a surfactant. The composition may exhibit a drug loading of about 30%-60% DFX, about 40%-60% DFX, about 30% DFX, 35% DFX, 40% DFX, 45% DFX, 50% DFX, 55% DFX, or 60% DFX. The composition may have less than about 1.0% degradation products of deferasirox (DFX). The DFX to pharmaceutical polymer ratio may be about 2:8 to about 7:3, including about 3:7, about 4:6, about 1:1, or about 6:4. The purity of DFX used in said composition may be about 95%, is about 99%, is about 99.5%, or is about 95% to about 100%. The purity of said composition may be about 95%, is about 99%, is about 99.5%, or is about 95% to about 100%. The pharmaceutical composition may comprise about 90 mg DFX, about 125 mg DFX, about 250 mg DFX, about 360 mg DFX, or about 500 mg DFX.

The pharmaceutical composition may comprise a second active pharmaceutical ingredient in addition to DFX, such as wherein the second active pharmaceutical ingredient is a second iron chelator, an agent used in the treatment or prevention of osteoporosis, an anti-fungal agent, or an agent that increases the rate of production of red blood cells, such as amphotericin B, deferiprone, deferoxamine, erythropoietin, or risedronate.

The one or more pharmaceutical polymers may comprise an agent selected from the group consisting of poly(vinyl acetate)-co-poly(vinylpyrrolidone) copolymer, ethylcellulose, hydroxypropylcellulose, cellulose acetate butyrate, poly(vinylpyrrolidone), poly(ethylene glycol), poly(ethylene oxide), poly(vinyl alcohol), hydroxypropyl methylcellulose, ethylcellulose, hydroxyethylcellulose, sodium carboxymethyl-cellulose, dimethylaminoethyl methacrylate-methacrylic acid ester copolymer, ethylacrylate-methylmethacrylate copolymer, cellulose acetate phthalate, cellulose acetate trimelletate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropylmethylcellulose acetate succinate and polyvinyl caprolactam-polyvinyl acetate-polyethylene glycol graft copolymer.

The surfactant may comprises an agent selected from the group consisting of sodium dodecyl sulfate, dioctyl sodium sulphosuccinate, polyoxyethylene (20) sorbitan monooleate, glycerol polyethylene glycol oxystearate-fatty acid glycerol polyglycol esters-polyethylene glycols-glycerol ethoxylate, glycerol-polyethylene glycol ricinoleate-fatty acid esters of polyethyleneglycol-polyethylene glycols-ethoxylated glycerol, vitamin E TPGS, and sorbitan laurate, and the pharmaceutical polymer comprises an agent selected from a group consisting of poly(vinylpyrrolidone), hydroxypropylcellulose, poly(vinyl alcohol), hydroxypropyl methylcellulose, hydroxyethylcellulose, and sodium carboxymethylcellulose, and polyvinyl caprolactam-polyvinyl acetate-polyethylene glycol graft copolymer.

The pharmaceutical composition may or may not contain a processing agent, such as a plasticizer. The composition may be a composite and may be a homogenous, heterogeneous, or heterogeneously homogenous composition. The one or more pharmaceutical polymers is/are a water soluble polymer(s), such as water soluble polymers selected from the group consisting of poly(vinyl acetate)-co-poly(vinylpyrrolidone) copolymer, poly(vinylpyrrolidone), cellulose acetate phthalate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropyl methylcellulose, hydroxypropylmethylcellulose acetate succinate, poly (vinyl alcohol), and polyvinyl caprolactam-polyvinyl acetate-polyethylene glycol graft copolymer. The DFX to water soluble pharmaceutical polymer ratio may be about 1:2, about 2:3, about 1:1. About 3:2 or about 2:1. The one or more pharmaceutically acceptable excipients may comprise a pharmaceutical polymer of high melt viscosity. The one or more pharmaceutically acceptable excipients may comprise a thermally labile pharmaceutical polymer.

The pharmaceutical composition may exhibit a peak solubility of the DFX in the composition of greater than 400-600 µg/mL, in an aqueous buffer with a pH range of 4 to 8, such as 400, 425, 450, 475, 500, 525, 550, 575 or 600 µg/mL. The peak solubility of the DFX and the reference standard DFX after an 8 hr dissolution test in an aqueous buffer with a pH range of 4 to 8 may have a ratio of greater than 4:1. The AUC of the DFX in the composition and AUC of the reference standard DFX may have a ratio that is greater than 4:3, such as 5:3, 2:1, 7:3 and 4:1. The pharmaceutical composition may have at least about 97% drug potency of deferasirox (DFX) as compared to the unprocessed deferasirox (DFX).

The pharmaceutical composition may be formulated as an oral dosage form, such as a tablet, a capsule, or a sachet, wherein the tablet may be a round flat tablet, a round concave tablet, an elongated tablet, or a minitab. The oral dosage form may be an extended release form or an immediate release form. The oral dosage form is a disintegrating tablet or an eroding tablet.

Also provided is pharmaceutical composition produced by a process comprising the steps of (a) providing crystalline deferasirox (DFX) and one or more pharmaceutically acceptable excipients; (b) compounding the materials of step (a) in a thermokinetic mixer for less than about 300 seconds and at less than or equal to about 200° C., wherein the thermokinetic compounding of DFX and the one or more pharmaceutically acceptable excipients forms a melt blended pharmaceutical composition. The one or more pharmaceutically acceptable excipients may include one or more water soluble pharmaceutical polymers, such as poly(vinyl acetate)-co-poly(vinylpyrrolidone) copolymer, poly(vinylpyrrolidone), cellulose acetate phthalate, poly(vinyl acetate) phthalate, hydroxypropylmethylcellulose phthalate, poly(methacrylate ethylacrylate) (1:1) copolymer, poly (methacrylate methylmethacrylate) (1:1) copolymer, poly (methacrylate methylmethacrylate) (1:2) copolymer, hydroxypropyl methylcellulose, hydroxypropylmethylcellulose acetate succinate, poly(vinyl alcohol), or polyvinyl caprolactam-polyvinyl acetate-polyethylene glycol graft copolymer. The composition may be a nanocomposite, or may be a partially or wholly amorphous dispersion. Step (b) may comprise compounding the materials of step (a) in a thermokinetic mixer for less than about 240 seconds, less than about 180 seconds, less than about 120 second, less than about 90 seconds, less than about 60 seconds, or less than about 30 seconds.

The pharmaceutical composition may comprise a surfactant. The pharmaceutical composition may be co-processed with second active pharmaceutical ingredient, such as wherein the second active pharmaceutical ingredient is a second iron chelator, an agent used in the treatment or prevention of osteoporosis, an anti-fungal agent, or an agent that increases the rate of production of red blood cells, such as amphotericin B, deferiprone, deferoxamine, erythropoietin, or risedronate.

The pharmaceutical composition may remain amorphous per x-ray diffraction analysis following storage in an open container at about 40° C., relative humidity of about 75%, at five weeks. The pharmaceutical composition may comprise about 30%-60% DFX, about 40%-60% DFX, about 30% DFX, 35% DFX, 40% DFX, 45% DFX, 50% DFX, 55% DFX, or 60% DFX. The purity of the composition may be about 95%, is about 99%, is about 99.5%, or is about 95% to about 100%. The purity of DFX used in said composition may be about 95%, is about 99%, is about 99.5%, or is about 95% to about 100%. Step (b) may be performed at a temperature of about 100° C., about 125° C., about 150° C., about 180° C., or about 100° C. to 200° C. The composition may have a single glass transition temperature.

In addition, there is provided a pharmaceutical composition comprising an amorphous dispersion of deferasirox (DFX) and one or more pharmaceutically acceptable excipients thermally processed into a composite, wherein the composite has less than about 1.0% degradation products of deferasirox (DFX). The pharmaceutical composition has less than about 0.5% degradation products of DFX, less than about 0.25% degradation products of DFX, or less than about 0.1% degradation products of DFX. The pharmaceutical composition may not comprise a processing agent. The composition may be formulated as an oral dosage form, such as a tablet, a capsule, sachet or a pellet. The tablet may be a round flat tablet, a round concave tablet, an elongated tablet, or a minitab. The oral dosage form may be an extended release form or an immediate release form. The oral dosage form is a disintegrating tablet or an eroding tablet.

The composition may remain amorphous per x-ray diffraction analysis following storage in an open container at about 40° C., relative humidity of about 75%, at five weeks. The composition may comprise about 30%-60% DFX, about 40%-60% DFX, about 30% DFX, 35% DFX, 40% DFX, 45% DFX, 50% DFX, 55% DFX, or 60% DFX. The pharmaceutical composition may exhibit a peak solubility of the DFX in the composition of greater than 400-600 µg/mL, in an aqueous buffer with a pH range of 4 to 8, such as 400, 425, 450, 475, 500, 525, 550, 575 or 600 µg/mL. The peak solubility of the DFX and the reference standard DFX after an 8 hr dissolution test in an aqueous buffer with a pH range of 4 to 8 may have a ratio of greater than 4:1. The AUC of the DFX in the composition and AUC of the reference standard DFX may have a ratio that is greater than 4:3.

The one or more pharmaceutically acceptable excipients may include one or more water soluble pharmaceutical polymers, such as poly(vinyl acetate)-co-poly(vinylpyrrolidone) copolymer, poly(vinylpyrrolidone), cellulose acetate phthalate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropyl methylcellulose, hydroxypropylmethylcellulose acetate succinate, poly(vinyl alcohol), or polyvinyl caprolactam-polyvinyl acetate-polyethylene glycol graft copolymer. The DFX to water soluble pharmaceutical polymer ratio may be about 1:2, about 2:3, about 1:1, about 3:2, or about 2:1. The pharmaceutical composition may comprise about 90 mg DFX, about 125 mg DFX, about 250 mg DFX, about 360 mg DFX, or about 500 mg DFX. The composition may have a single glass transition temperature.

In further embodiments, there are provided:
a pharmaceutical composition comprising an amorphous dispersion of deferasirox (DFX) and one or more pharmaceutically acceptable excipients thermally processed into a composite, wherein the composition which does not have substantial degradation of deferasirox (DFX) and each excipient;

a pharmaceutical composition comprising an amorphous dispersion of deferasirox (DFX) and one or more pharmaceutically acceptable excipients thermally processed into a composite, wherein the composition which has less than about 1.0% degradation products of deferasirox (DFX), does not have substantial degradation of each excipient, and the composition does not comprise a processing agent;

a pharmaceutical composition comprising an amorphous dispersion of deferasirox (DFX) and one or more pharmaceutically acceptable excipients thermally processed into a composite, wherein the composition which has less than about 1.0% degradation products of deferasirox (DFX), and the composition does not comprise a processing agent;

a pharmaceutical composition comprising an amorphous dispersion of deferasirox (DFX) and one or more pharmaceutically acceptable excipients thermally processed into a composite, in which the composite exhibits a single glass transition temperature, and which does not have substantial degradation of deferasirox (DFX), while a formulation of deferasirox (DFX) and identical pharmaceutically acceptable excipients processed thermally by a process other than thermokinetic compounding exhibits two or more glass transition temperatures; and a pharmaceutical composition comprising an amorphous dispersion of deferasirox (DFX) and one or more pharmaceutically acceptable excipients thermally processed into a composite, in which the glass transition temperature is significantly higher than the glass transition temperature of a formulation of deferasirox (DFX) and identical pharmaceutically acceptable excipients processed thermally by a process other than thermokinetic compounding, and which does not have substantial degradation of deferasirox (DFX), and wherein the composition does not comprise a processing agent.

The pharmaceutical composition of any of the preceding embodiments may have at least about 97% drug potency of deferasirox (DFX) as compared to the unprocessed deferasirox (DFX). The pharmaceutical composition may be formulated as an oral dosage form. The oral dosage form may be a tablet, a capsule, sachet or a pellet. The tablet may be a round flat tablet, a round concave tablet, an elongated tablet, or a minitab. The oral dosage form may be an extended release form or an immediate release form. The oral dosage form may be a disintegrating tablet or an eroding tablet.

The pharmaceutical composition may remain amorphous per x-ray diffraction analysis following storage in an open container at about 40° C., relative humidity of about 75%, at five weeks. The composition may comprise about 30%-60% DFX, about 40%-60% DFX, about 30% DFX, 35% DFX, 40% DFX, 45% DFX, 50% DFX, 55% DFX, or 60% DFX. The pharmaceutical composition may exhibit a peak solubility of the DFX in the composition of greater than 400-600 μg/mL, in an aqueous buffer with a pH range of 4 to 8, such as 400, 425, 450, 475, 500, 525, 550, 575 or 600 μg/mL. The peak solubility of the DFX and the reference standard DFX after an 8 hr dissolution test in an aqueous buffer with a pH range of 4 to 8 may have a ratio of greater than 4:1. The AUC of the DFX in the composition and AUC of the reference standard DFX may have a ratio that is greater than 4:3.

The one or more pharmaceutically acceptable excipients may include one or more water soluble pharmaceutical polymers, such as poly(vinyl acetate)-co-poly(vinylpyrrolidone) copolymer, poly(vinylpyrrolidone), cellulose acetate phthalate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropyl methylcellulose, hydroxypropylmethylcellulose acetate succinate, poly(vinyl alcohol), or polyvinyl caprolactam-polyvinyl acetate-polyethylene glycol graft copolymer. The DFX to water soluble pharmaceutical polymer ratio may be about 1:2, about 2:3, about 1:1, about 3:2, or about 2:1. The pharmaceutical composition may comprise about 90 mg DFX, about 125 mg DFX, about 250 mg DFX, about 360 mg DFX, or about 500 mg DFX.

In addition, novel pharmaceutical compositions or composites made by TKC and discussed above may be further processed according to methods well known to those of skill in the art, including but not limited to compression molding, tablet compression, capsule filling, film-coating, or injection molding into a final product. In certain embodiments, the composite made by TKC is the final product. Another embodiment is directed to addition of DFX and one or more pharmaceutically acceptable excipients in a ratio of about 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, or 1:10. Yet another embodiment is directed to addition of DFX and one or more pharmaceutically acceptable adjuvants in a ratio of about 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, 1:10, 1:15, 1:20 1:25, 1:30, 1:40, 1:50, 1:60, 1:70, 1:80, 1:90, 1:100, 1:150, 1:200, 1:300, 1:400 or 1:500. An additional embodiment is directed to addition of DFX and one or more additional active pharmaceutical ingredient ("API"). The ratio of DFX to other API may be 20:1, 16:1, 6:1, 2:1, 1:1, 1:2, 1:6, 1:16, 1:20.

The thermokinetic processing may be conducted in a thermokinetic chamber. A thermokinetic chamber is an enclosed vessel or chamber in which TKC occurs. In one aspect, the average temperature inside the chamber is ramped up to a pre-defined final temperature over the duration of processing to achieve optimal thermokinetic mixing of DFX and the one or more pharmaceutically acceptable excipients, adjuvants, additional APIs, or any combination thereof, into a composite. In another aspect, multiple speeds are used during a single, rotationally continuous TKC operation to achieve optimal thermokinetic mixing of DFX and one or more pharmaceutically acceptable excipients, adjuvants, additional APIs, or any combination thereof, into a composite with minimal thermal degradation. The length of processing and exposure to elevated temperatures or speeds during thermokinetic mixing will generally be below the thermal sensitivity threshold of DFX, excipient(s), adjuvant(s), or additional API(s). In another aspect, the thermokinetic processing is performed at an average temperature at or below the melting point of DFX, excipient(s), adjuvant(s), or additional API(s); the thermokinetic processing is performed at an average temperature at or below the glass transition temperature of DFX, excipient(s), adjuvant(s), or additional API(s); or the thermokinetic processing is performed at an average temperature at or below the molten transition point of DFX, excipient(s), adjuvant(s), or additional API(s).

In certain embodiments, the thermokinetic processing substantially eliminates DFX, excipient, adjuvant or additional API degradation. For example, TKC may generate compositions and composites with less than about 2.0%, 1.0%, 0.75%, 0.5%, 0.1%, 0.05%, or 0.01% degradation products of DFX, adjuvant, excipient or additional API. In other embodiments, TKC may generate compositions with a minimum of at least about 90%, 91%, 92%, 93%, 94%, 95%, 96%, 97%, 98%, 99%, or 99.9% drug potency with respect to DFX. Examples of TKC may be performed for less than 5, 10, 15, 20, 25, 30, 35, 40, 45, 50, 55, 60, 75, 100, 120, 150, 180, 240 and 300 seconds. Generally, TKC may be performed for less than 5, 10, 15, 20, 25, 30, 35, 40, 45, 50, 55, 60, 75, 100, 120, 150, 180, 240 and 300 seconds, and any ranges therein. In certain embodiments, the DFX has an amorphous morphology.

In certain embodiments, the formulations may provide for enhanced solubility of DFX through the mixing of DFX with pharmaceutically acceptable polymers, carriers, surfactants, excipients, adjuvants or any combination thereof. Thus, for example, compositions which display enhanced solubility are comprised of DFX and a surfactant or surfactants, DFX and a pharmaceutical carrier (thermal binder) or carriers, or DFX and a combination of a surfactant and pharmaceutical carrier or surfactants and carriers.

A further embodiment of the present disclosure is a pharmaceutical composition comprising DFX and one or more pharmaceutically acceptable excipients, adjuvants, additional APIs, or a combination thereof, wherein greater than about 80% of the dose is dissolved within two hours after a media change from aqueous media of about pH 1.2 to an aqueous buffer of pH between 4 and 8.

A further embodiment of the present disclosure is a pharmaceutical composition comprising DFX and one or more pharmaceutically acceptable excipients, adjuvants, additional APIs, or a combination thereof, wherein a ratio of peak solubility of DFX in the composition over peak solubility of the reference standard DFX, is greater than about 2:1, 3:1, about 4:1, about 5:1, about 6:1, about 7:1, about 8:1, about 9:1, or about 10:1.

A further embodiment of the present disclosure is a pharmaceutical composition comprising DFX and one or more pharmaceutically acceptable excipients, adjuvants, or additional APIs, wherein AUC of the DFX in the composition and AUC of the reference standard DFX, when delivered orally have a ratio that is greater than about 4:3, 5:3, 2:1, or about 5:1.

A further embodiment of the present disclosure is a method of formulating a pharmaceutical composition comprising DFX and one or more pharmaceutically acceptable excipients, adjuvants, additional APIs, or any combination thereof, by TKC to increase bioavailability of the DFX, comprising thermokinetic processing of the DFX with the one or more pharmaceutically acceptable excipients, adjuvants, additional APIs, or any combination thereof until melt blended into a composite.

A further embodiment of the present disclosure is a pharmaceutical composition comprising DFX and one or more pharmaceutically acceptable excipients, adjuvants, additional APIs, or any combination thereof, wherein the composition is a homogenous, heterogenous, or heterogeneously homogenous composition which has a single glass transition temperature.

A further embodiment of the present disclosure is a pharmaceutical composition comprising DFX and one or more pharmaceutically acceptable excipients, adjuvants, additional APIs, or any combination thereof, processed into a composite, wherein the composite is a homogenous, heterogenous, or heterogeneously homogenous composition which has a less than about 1.0%, about 2%, about 3%, about 4% or about 5%, about 6%, about 7%, about 8%, about 9%, or about 10% degradation products of the DFX.

A further embodiment of the present disclosure is particle size reduction of DFX in an excipient carrier system in which DFX is not miscible, not compatible, or not miscible or compatible. Particle size reduction can be achieved by attrition of the API particles according to the mechanical forces imparted by the TKC process with simultaneous mixing with the molten excipient carrier. Particle size reduction can also be achieved by melting DFX with the carrier at elevated temperature by TKC processing and subsequently forcing recrystallization of DFX as fine particles in the carrier upon quenching. By this method, a secondary annealing step may also be required to bring the recrystallization process to completion. In one aspect, DFX is in the form of a nanocomposite with the excipient carrier system.

The novel pharmaceutical compositions or composites made by TKC and disclosed herein may be administered to a treat a mammal, including without limitation a human patient or subject, to reduce chronic iron overload in subjects, for example in subjects who are receiving long-term blood transfusions for conditions such as a blood disorder, including but not limited to β-thalassemia, non-transfusion-dependent thalassemia (NTDT) syndrome and other chronic anemias. The chronic iron overload can be due to blood transfusions, particularly in patients 2 years of age and older. In certain embodiments, such compositions or composites may be used in a method of treating a subject who experiences a suboptimal or inadequate response to maximum approved doses of currently available DFX formulations (e.g., Exjade®, Desirox®, Defrijet®, Desifer®, Jadenu®). Such suboptimal or inadequate response may result in such subjects not achieving negative iron balance. Subjects that may be treated by such compositions or composites include children, juveniles, young adults and adults of any age. In particular embodiments, the bioavailability of such compositions or composites are independent of a food effect. For example, the bioavailable of such compositions or composites are independent of any consumption by a subject of a high fat meal prior to, with, or shortly after administration of such compositions or composites. The administration of the pharmaceutical composition to the mammal may result in an AUC value that is statistically equivalent regardless of whether the subject has fasted or has consumed a high fat meal immediately prior to administration of the composition.

Also provided are pharmaceutical compositions comprising an amorphous dispersion of deferasirox (DFX) and one or more pharmaceutically acceptable excipients thermally processed into a composite by thermokinetic compounding, in which the composite is a single phase, amorphous composite, wherein at least one of the pharmaceutically acceptable excipients is immiscible with DFX when thermally processed by a process other than thermokinetic compounding.

In particular, there is provided a method of treating a subject for chronic iron overload in a subject who experiences a suboptimal or inadequate response to non-amorphous dispersions or crystalline forms of deferasirox (DFX) comprising administering to the subject a pharmaceutical composition comprising an amorphous dispersion of DFX and one or more pharmaceutically acceptable excipients. The amorphous dispersion of DFX may be thermally processed into a composite by thermokinetic compounding, and the non-amorphous dispersion or crystalline form of DFX may be thermally processed by a process other than thermokinetic compounding. The may have a blood disorder, such as β-thalassemia, non-transfusion-dependent thalassemia (NTDT) syndrome or chronic anemia. The bioavailability of the amorphous dispersion of DFX may be independent of any food effect, such as a food effect from consuming a high fat meal.

Still further there is provided a pharmaceutical composition comprising deferasirox (DFX) and one or more pharmaceutically acceptable excipients thermally processed into a composite by thermokinetic compounding, wherein administration of the composition to fasted human subjects provides an $AUC_{0-T}$ value is at least 15% greater when compared to administration of a pharmaceutical composition comprising DFX and one or more pharmaceutically acceptable excipients thermally processed by a process other than thermokinetic compounding. The $AUC_{0-T}$ value may be at least 25% greater.

Also provided is a pharmaceutical composition comprising deferasirox (DFX) and one or more pharmaceutically acceptable excipients thermally processed into a composite by thermokinetic compounding, wherein administration of the composition to human subjects provides an AUC increase of at least 50% when compared to administration of a pharmaceutical composition comprising DFX and one or more pharmaceutically acceptable excipients thermally processed by a process other than thermokinetic compounding.

Also provided is a pharmaceutical composition comprising deferasirox (DFX) and one or more pharmaceutically acceptable excipients thermally processed into a composite by thermokinetic compounding, wherein administration of the composition to fasted human subjects provides a $C_{max}$ standard deviation of less than 30% and an $AUC_{0-\infty}$ standard deviation of less than 35%.

BRIEF DESCRIPTION OF THE DRAWINGS

The U.S. patent or application file contains at least one drawing executed in color. Copies of the U.S. patent or patent application publication with color drawing(s) will be provided by the office by request and payment of the necessary fees.

The following drawings form part of the present specification and are included to further demonstrate certain aspects of the present disclosure. The disclosure may be better understood by reference to one or more of these drawings in combination with the detailed description of specific embodiments presented herein.

(60% API, 40% Copovidone) amorphous intermediate, equivalent to 360 mg DFX total; 47—Two capsules containing lot 13-004-47 (50% API, 33.33% Copovidone, 16.67% HPMCAS L) amorphous intermediate, equivalent to 360 mg DFX total; 50—Two capsules containing lot 13-004-50 (40% API, 60% Eudragit L100-55) amorphous intermediate, equivalent to 360 mg DFX total; 57—Two capsules containing lot 13-004-57 (40% API, 30% Copovidone, 30% Eudragit L100-55) amorphous intermediate, equivalent to 360 mg DFX total; 58—Two capsules containing lot 13-004-58 (50% API, 50% Copovidone) amorphous intermediate, equivalent to 360 mg DFX total; 39—Two capsules containing lot 13-004-39 (60% API, 40% Copovidone) partially crystalline intermediate, equivalent to 360 mg DFX total.

Figure 14:
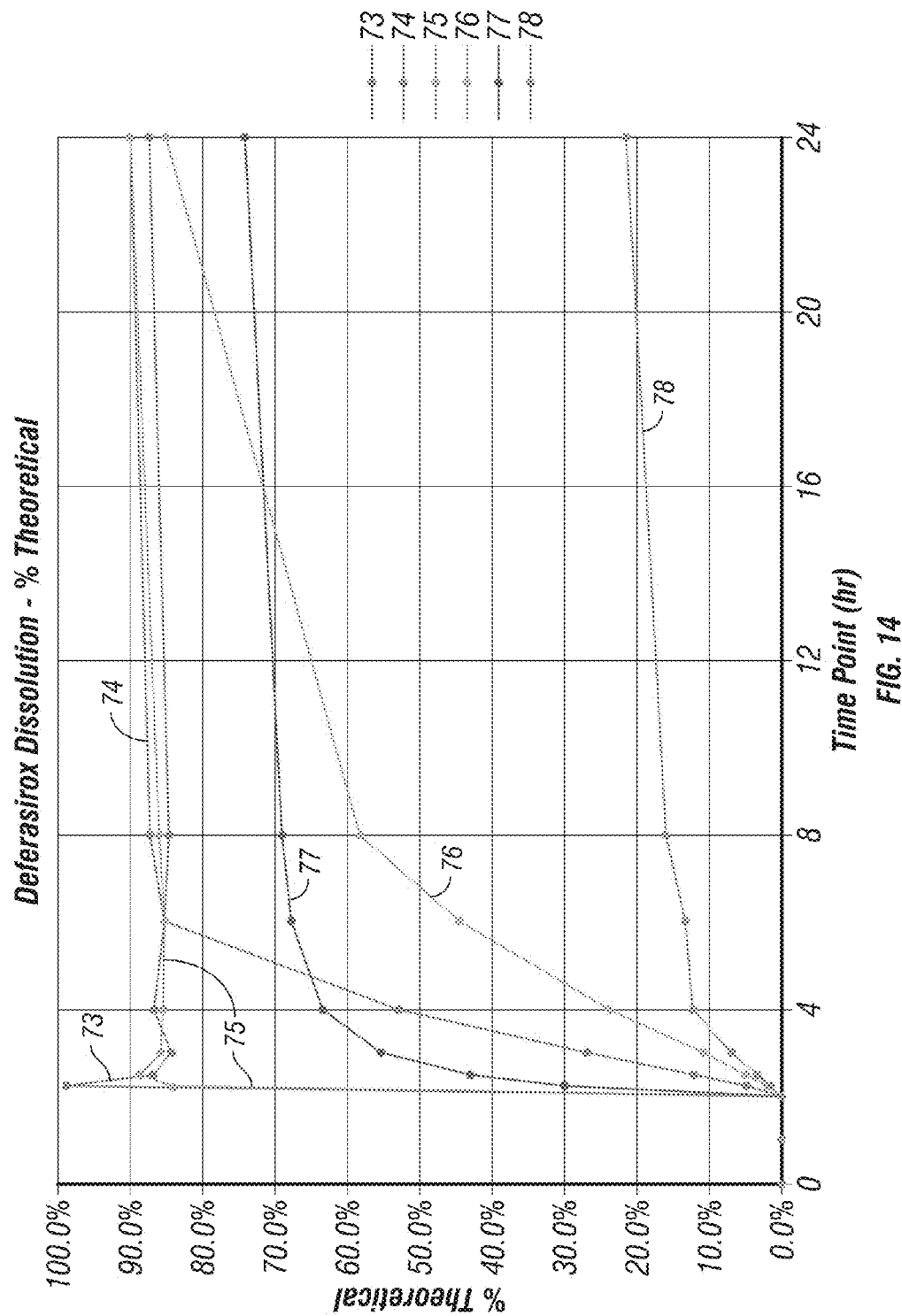

FIG. 14. Dissolution profiles of disintegrating and eroding tablets containing amorphous intermediates. 73—Tablet lot 13.004.73, disintegrating tablet containing lot 13-004-58 (50% API, 50% Copovidone) amorphous intermediate; 74—Tablet lot 13.004.74, eroding tablet containing lot 13-004-58 (50% API, 50% Copovidone) amorphous intermediate; 75—Tablet lot 13.004.75, disintegrating tablet containing lot 13-004-60 (50% API, 25% Copovidone, 25% Eudragit L100-55) amorphous intermediate; 76—Tablet lot 13.004.76, eroding tablet containing lot 13-004-60 (50% API, 25% Copovidone, 25% Eudragit L100-55) amorphous intermediate; 77—Tablet lot 13.004.77, disintegrating tablet containing lot 13-004-50 (40% API, 60% Eudragit L100-55) amorphous intermediate; 78—Tablet lot 13.004.78, eroding tablet containing lot 13-004-50 (40% API, 60% Eudragit L100-55) amorphous intermediate.

Figure 15:
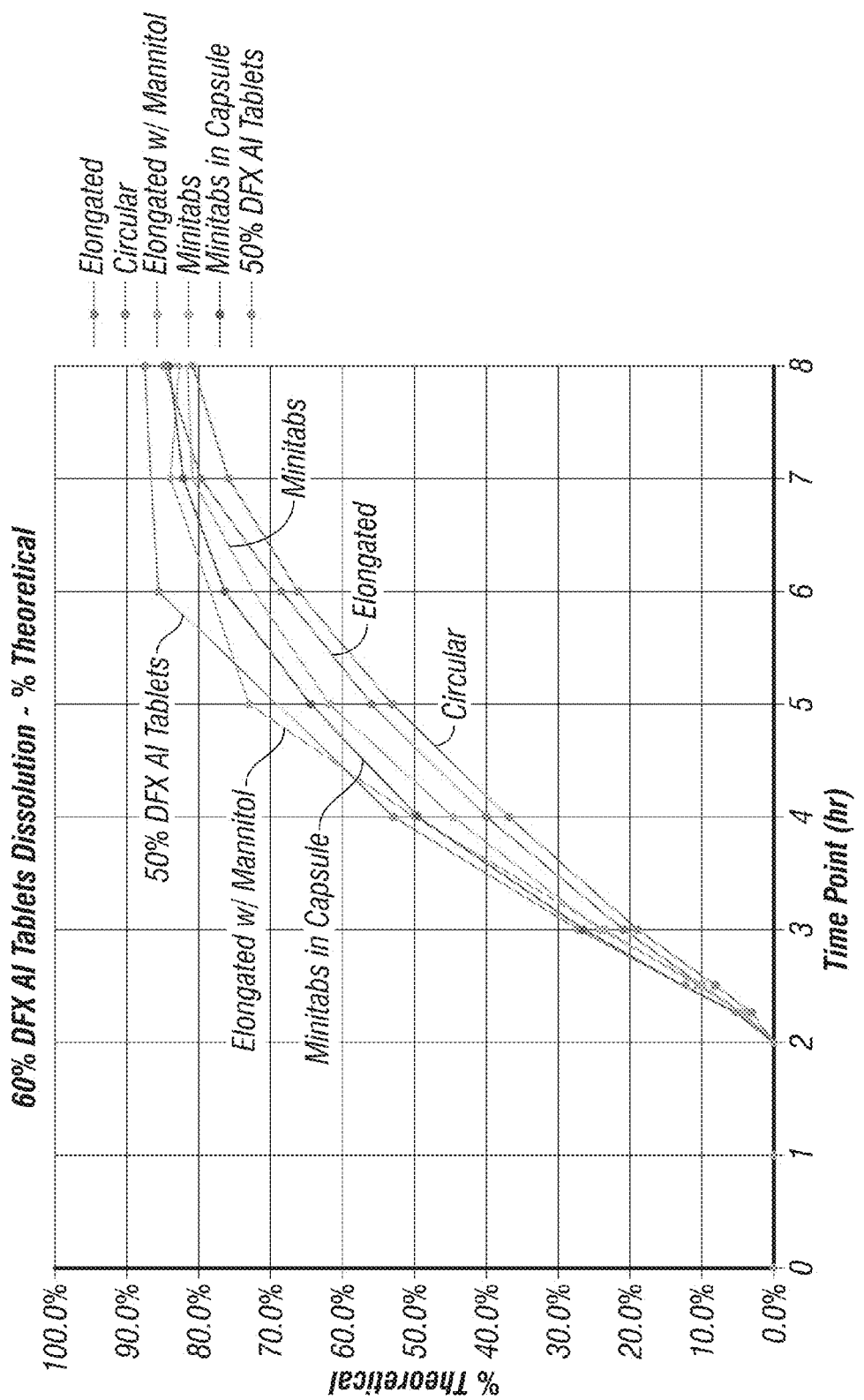

FIG. 15. Dissolution profiles of eroding tablets with different geometries containing lot 13-004-40 (60% API, 40% Copovidone) amorphous intermediate. Elongated: Tablet lot 13.004.84 #1, one tablet; Circular: Tablet lot 13.004.84 #2, one tablet; Elongated w/Mannitol: Tablet lot 13.004.84 #3, one tablet; Minitabs: Tablet lot 13.004.84 #4, three tablets; Minitabs in Capsule: Tablet lot 13.004.84 #4, three tablets filled into a size 00 capsule; 50% DFX AI tablets: Reference; tablet lot 13.004.74, one tablet containing lot 13-004-58 (50% API, 50% Copovidone) amorphous intermediate.

Figure 16:
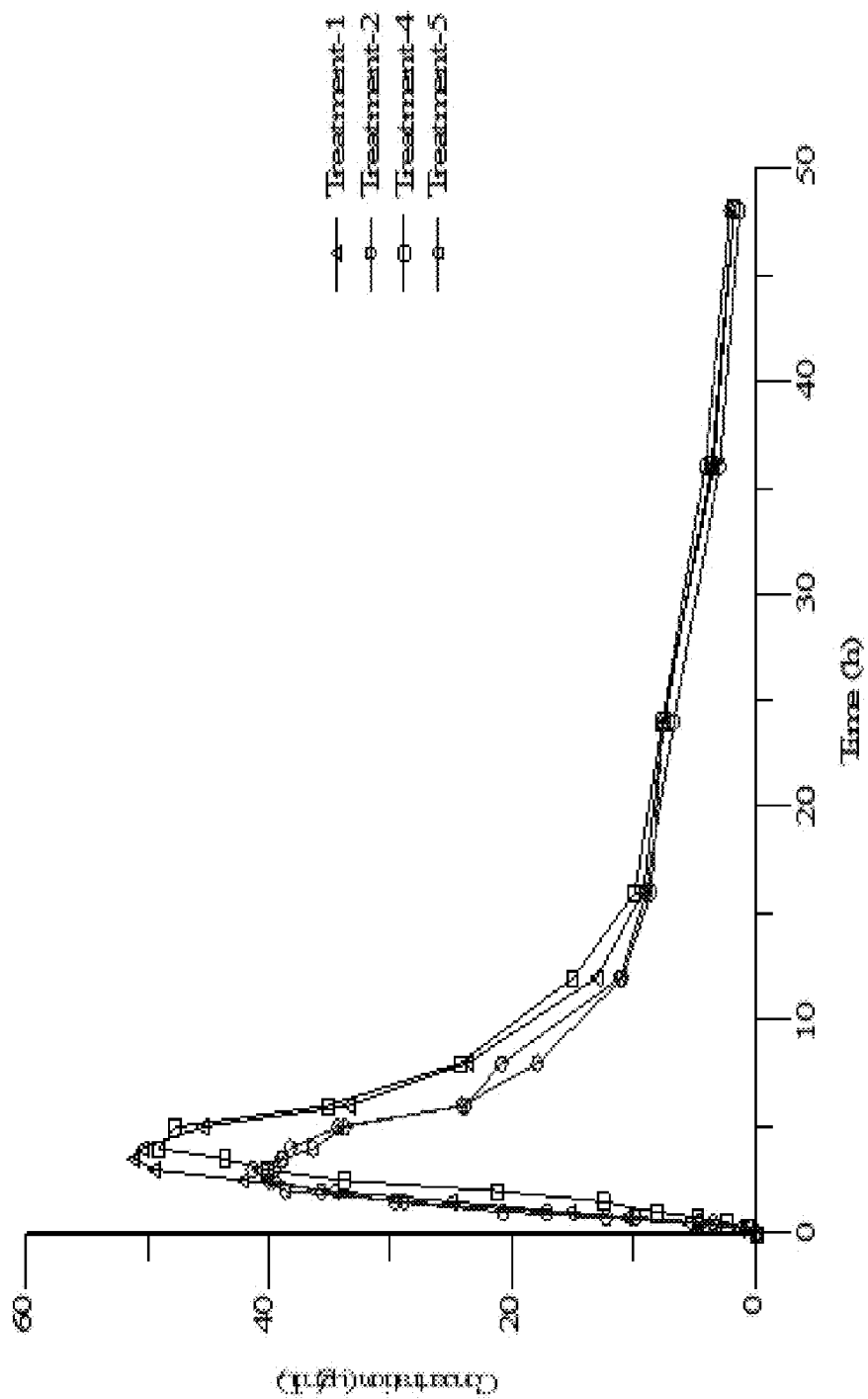

FIG. 16. Plasma concentration versus time plots for Treatment 1 (Formulation 30011, fasted), Treatment 2 (Jadenu® reference, fasted), Treatment 4 (Formulation 30012, fasted) and Treatment 5 (Jadenu® reference, fasted).

Figure 17:
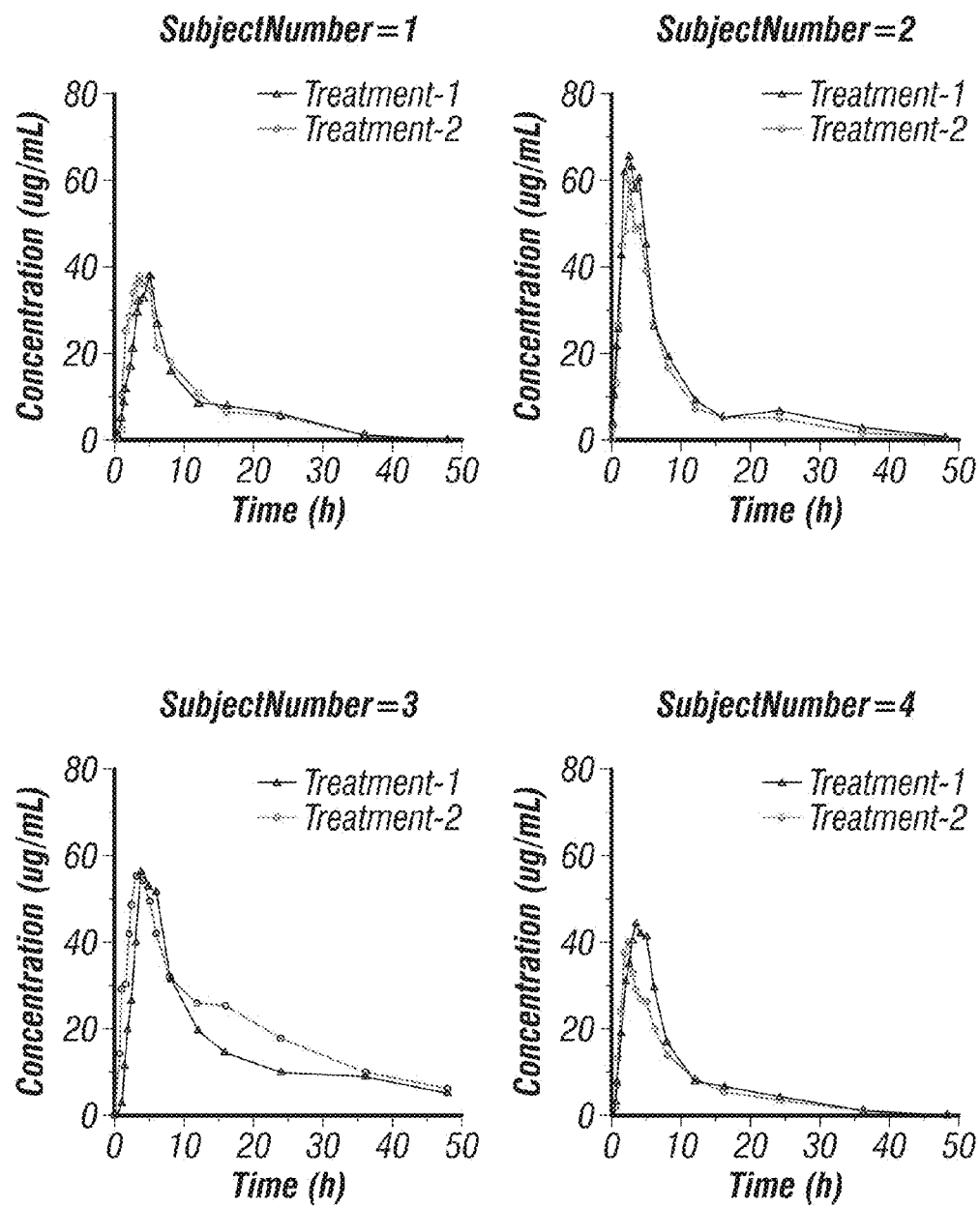
Figure 17:
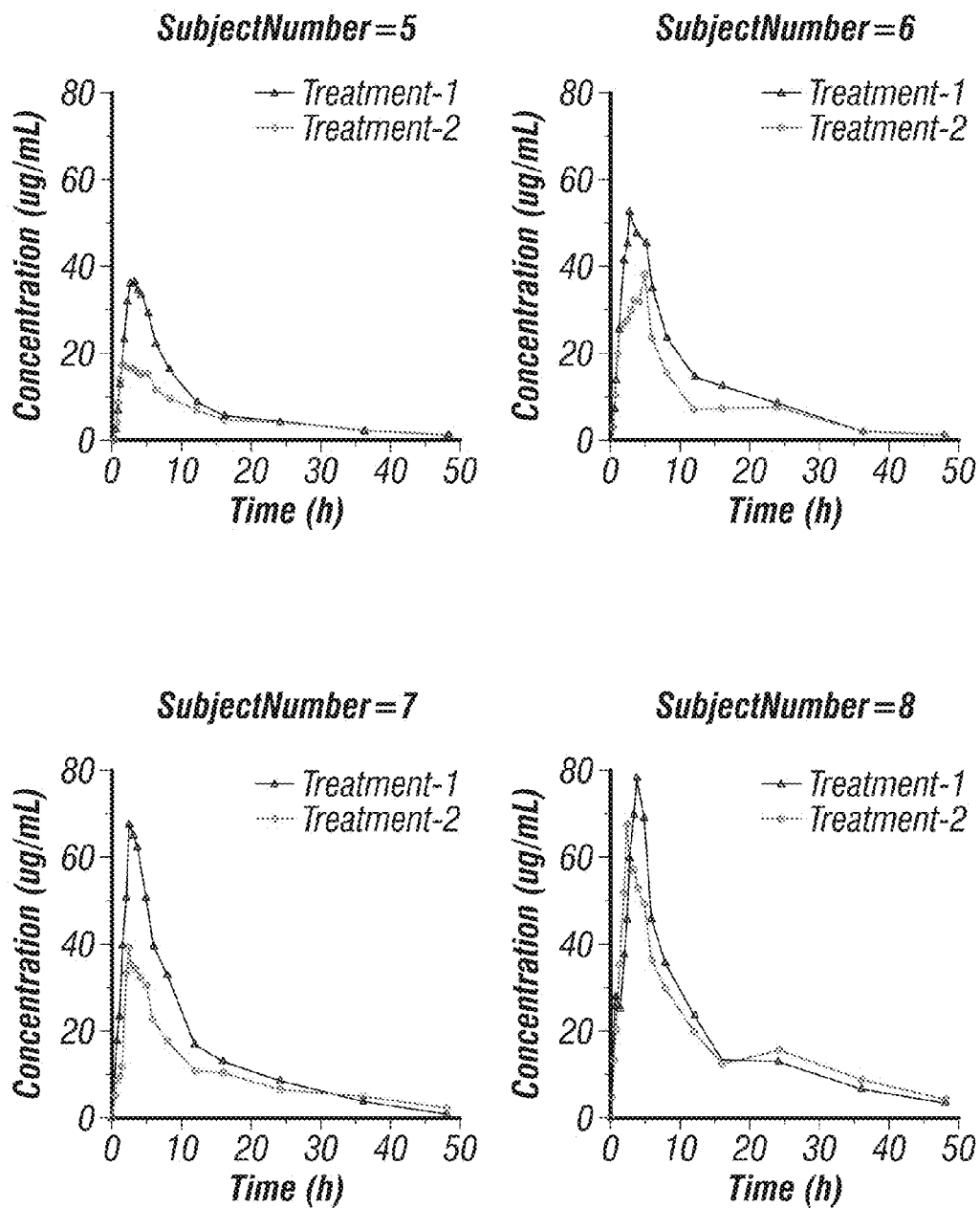
Figure 17:
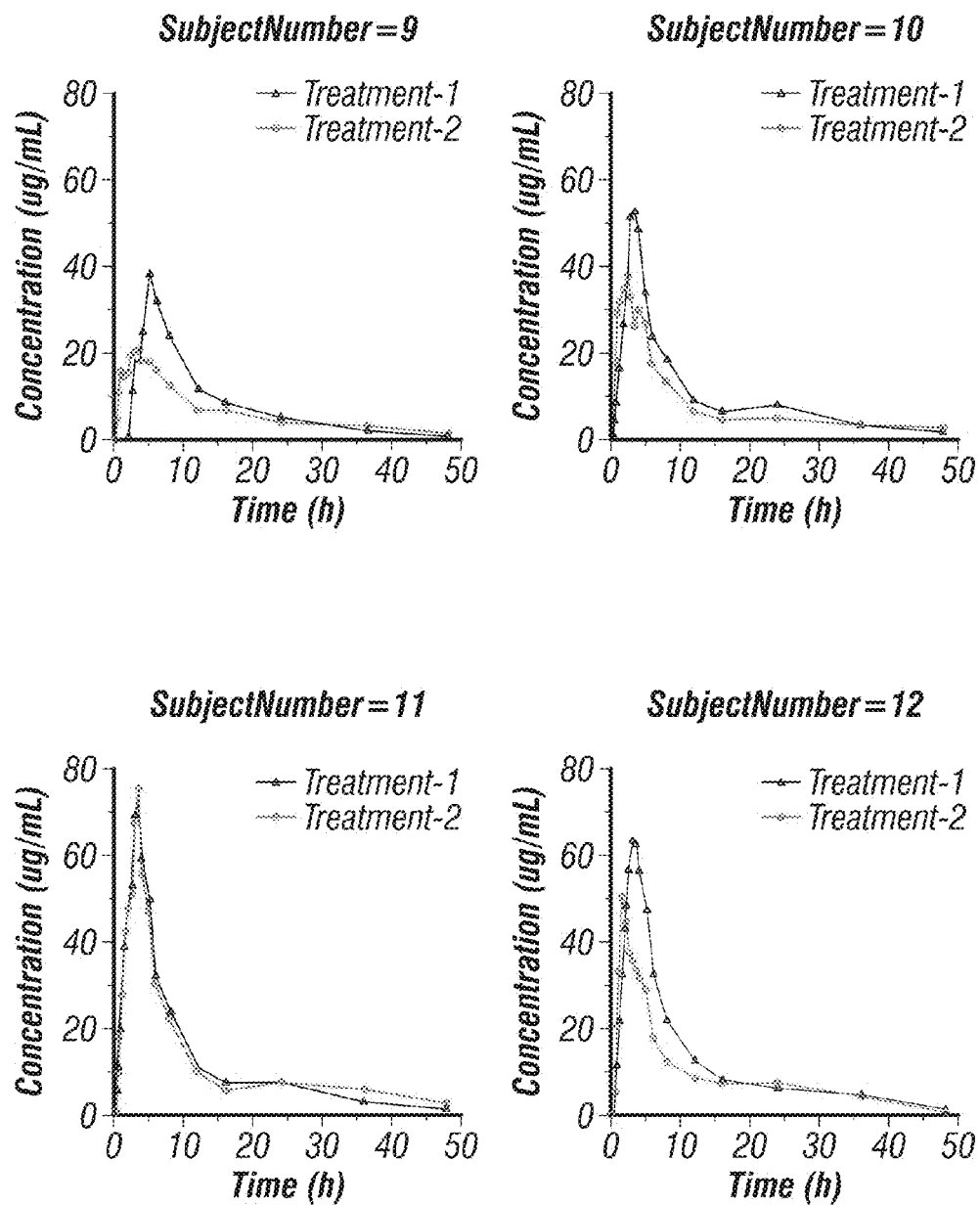

FIG. 17. Individual subjects' plasma DFX concentration versus time curves for Treatment 1 (Formulation 30011, fasted) versus Treatment 2 (Jadenu® reference, fasted).

DETAILED DESCRIPTION

Although making and using various embodiments of the present disclosure are discussed in detail below, it should be appreciated that the present disclosure provides many inventive concepts that may be embodied in a wide variety of contexts. The specific aspects and embodiments discussed herein are merely illustrative of ways to make and use the disclosure, and do not limit the scope of the disclosure.

Described herein are improved deferasirox (DFX) compositions and methods for their manufacture. The methods permit thermal processing to produce an amorphous solid dispersion of DFX with high amorphous drug loading. The high melting point of DFX precludes the use of other thermal processing technologies, namely melt extrusion, for the production the amorphous dispersion compositions described herein because the processing temperatures required to achieve high-drug load DFX amorphous dispersions would exceed the degradation temperatures of the polymers. Moreover, the prolonged processing times of a typical melt extrusion process at the temperatures required to form a high drug load DFX amorphous dispersion are expected to result in the generation of high drug-related impurities content (>1%). Moreover, the non-solvent nature of the methods eliminates issues associated with solvent-based processes, namely, cost, safety, and environmental waste. Further, the methods are vastly more efficient than the leading solvent-based processes; namely, spray drying; owing to the limited solubility of DFX in common volatile organic solvents, which leads to copious amounts of solvent evaporation to obtain a relatively small amount of solids. The methods of the current disclosure permit unique amorphous dispersion compositions of DFX with an array of pharmaceutical carriers including ionic, non-ionic, cross-linked, highly viscous, and thermally labile pharma polymers with additional advantages in drug manufacture and delivery.

Using the processing methods described herein, enhanced dissolution kinetics and mitigation of pH-dependent solubility of DFX by the amorphous solid dispersion formulations are achieved, resulting in improved pharmacokinetic (PK) profiles relative to compositions containing crystalline DFX. For example, increased total oral absorption (AUC) of DFX, increased peak plasma concentrations ($C_{max}$) of DFX, reduced PK variability, mitigated food effect, complete and consistent absorption in human subjects relative to compositions containing crystalline DFX, and enhanced DFX efficacy in patients that poorly absorb crystalline forms of the compound are all achieved.

Tens of thousands of transfusion-dependent (e.g., thalassemia) patients worldwide suffer from chronic iron overload and its potentially fatal complications. DFX, commercially available in many countries since 2006, has been a major advance for patients with transfusional hemosiderosis, a proportion of patients have suboptimal response to the maximum approved doses (30 mg/kg per day), and do not achieve negative iron balance. Chirnomas et al. (2009) reported a prospective study of oral deferasirox pharmacokinetics (PK), comparing 10 transfused patients with inadequate deferasirox response (rising ferritin trend or rising liver iron on deferasirox doses >30 mg/kg per day) with control transfusion-dependent patients with adequate response. Patients with inadequate response to deferasirox had significantly lower systemic drug exposure compared with control patients. $C_{max}$, volume of distribution/bioavailability (Vd/F), and elimination half-life ($t_{(1/2)}$) were not different between the groups, suggesting bioavailability as the likely discriminant.

Since the DFX dissolution and solubility enhancement achieved with the compositions described herein are superior to the currently available compositions, these new formulations will enable therapeutic concentrations to be achieved at substantially lower doses in patients that have been previously identified to be inadequate responders to DFX when administered orally in a substantially crystalline form. This will improve the efficacy of DFX in these patients by achieving therapeutic blood levels at reasonable doses and enabling more rapid and consistent dose titration, as well as improve the safety profile of DFX in these patients as these formulations will substantially reduce the administered dose and consequently the frequency and severity of adverse events.

These and other aspects of the disclosure are discussed in detail below.

I. Definitions

To facilitate the understanding of this disclosure, a number of terms are defined below. Terms defined herein have meanings as commonly understood by a person of ordinary skill in the areas relevant to the present disclosure. Terms such as "a", "an" and "the" are not intended to refer to only a singular entity, but include the general class of which a specific example may be used for illustration.

With regard to the values or ranges recited herein, the term "about" is intended to capture variations above and below the stated number that may achieve substantially the same results as the stated number. In the present disclosure, each of the variously stated ranges is intended to be continuous so as to include each numerical parameter between the stated minimum and maximum value of each range. For example, a range of about 1 to about 4 includes about 1, 1, about 2, 2, about 3, 3, about 4, and 4. The terminology herein is used to describe specific embodiments of the disclosure, but their usage does not delimit the disclosure, except as outlined in the claims.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, the term "thermokinetic compounding" or "TKC" refers to a method of thermokinetic mixing until melt blended. TKC may also be described as a thermokinetic mixing process or thermokinetic processing in which processing ends at a point sometime prior to agglomeration. The commercial name for this process is "KinetiSol®".

As used herein, the phrase "a homogenous, heterogenous, or heterogeneously homogenous composite or an amorphous composite" refers to the various compositions that can be made using the TKC method.

As used herein, the term "heterogeneously homogenous composite" refers to a material composition having at least two different materials that are evenly and uniformly distributed throughout the volume.

As used herein, the phrase "reference standard active pharmaceutical ingredient" means the most thermodynamically stable form of the active pharmaceutical ingredient that is currently available.

As used herein, the term "substantial degradation," in conjunction with the term "DFX" or "additional API(s)" refers to degradation leading to the generation of impurities at levels beyond the threshold that has been qualified by toxicology studies, or beyond the allowable threshold for unknown impurities. See, for example Guidance for Industry, Q3B(R2) Impurities in New Drug Products (International Committee for Harmonization, published by the U.S. Department of Health and Human Services, Food and Drug Administration, Center for Drug Evaluation and Research (CDER), Center for Biologics Evaluation and Research, July, 2006. As used herein, the term "substantial degradation," in conjunction with the term "excipient" refers to decomposition of the excipient to the extent that the excipient would no longer meet the specifications set forth in an official monograph of an accepted pharmacopeia, e.g., the United States Pharmacopeia.

As used herein, the term "high melt viscosity" refers to melt viscosities greater than 10,000 Pa*s.

As used herein, the term "thermally labile API" refers to an API that degrades at its crystalline melting point, or one that degrades at temperatures below the crystalline melting point when in a non-crystalline (amorphous) form. As used herein, the term "thermolabile polymer" refers to a polymer that degrades at or below about 200° C.

Whether the composition of the present disclosure is a homogenous, heterogenous, or heterogeneously homogenous composition, an amorphous composition or combinations thereof, the TKC processing conditions can produce a composition with a glass transition temperature that is higher than the glass transition temperature of an identical combination of the drug and pharmaceutically acceptable excipients, adjuvants, additional APIs, or any combination thereof, thermally processed or processed using the MBP method, for example either with or without the use of a plasticizer. The TKC processing conditions can also produce a composition with a single glass transition temperature, wherein an identical combination of the identical API and pharmaceutically acceptable excipients, adjuvants, additional APIs, or any combination thereof, processed thermally has two or more glass transition temperatures. In other embodiments, the pharmaceutical compositions of the present disclosure have a single glass transition temperature that is at least about 20%, 30%, 40%, 50%, 60%, 70%, 80%, or 90% higher than the lowest glass transition temperature of the identical combination processed thermally. Alternatively, the compositions made using thermokinetic processing may generate compositions with a minimum of at least about 90%, 91%, 92%, 93%, 94%, 95%, 96%, 97%, 98%, 99%, or 99.9% therapeutic potency with respect to each drug.

As used herein, the term "thermokinetic chamber" refers to an enclosed vessel or chamber in which the TKC method is used to make the novel compositions of the present disclosure.

As used herein, "thermally processed" or "processed thermally" means that components are processed by hot melt extrusion, melt granulation, compression molding, tablet compression, capsule filling, film-coating, or injection molding.

As used herein, "extrusion" is the well-known method of applying pressure to a damp or melted composition until it flows through an orifice or a defined opening. The extrudable length varies with the physical characteristics of the material to be extruded, the method of extrusion, and the process of manipulation of the particles after extrusion. Various types of extrusion devices can be employed, such as screw, sieve and basket, roll, and ram extruders. Furthermore, the extrusion can be carried out through melt extrusion. Components of the present disclosure can be melted and extruded with a continuous, solvent free extrusion process, with or without inclusion of additives. Such processes are well-known to skilled practitioners in the art.

As used herein, "spray congealing" is a method that is generally used in changing the structure of materials, to obtain free flowing powders from liquids and to provide pellets. Spray congealing is a process in which a substance of interest is allowed to melt, disperse, or dissolve in a hot melt of other additives, and is then sprayed into an air chamber wherein the temperature is below the melting point of the formulation components, to provide congealed pellets. Such a process is well-known to skilled practitioners in the art.

As used herein, "solvent dehydration" or "spray drying technique" is commonly employed to produce a dry powder from a liquid or slurry by rapidly drying with a hot gas. This is one preferred method of drying many thermally-sensitive materials such as foods and pharmaceuticals. Water or organic solvent based formulations can be spray dried by using inert process gas, such as nitrogen, argon and the like. Such a process is well-known to skilled practitioners in the art.

As used herein, "bioavailability" is a term meaning the degree to which a drug becomes available to the target tissue after being administered to the body. Poor bioavailability is a significant problem encountered in the development of pharmaceutical compositions, particularly those containing a drug that is not highly soluble.

As used herein, the phrase "pharmaceutically acceptable" refers to molecular entities, compositions, materials, excipients, carriers, and the like that do not produce an allergic or similar untoward reaction when administered to humans in general.

As used herein, "poorly soluble" refers to drug having a solubility such that the dose to be administered cannot be fully dissolved in 250 ml of aqueous media ranging in pH from 1 to 7.5, a drug with a slow dissolution rate, and a drug with a low equilibrium solubility, for example resulting in decreased bioavailability of the pharmacological effect of the therapeutic drug being delivered.

As used herein, "derivative" refers to chemically modified inhibitors or stimulators that still retain the desired effect or property of the original drug. Such derivatives may be derived by the addition, removal, or substitution of one or more chemical moieties on the parent molecule. Such moieties may include, but are not limited to, an element such as a hydrogen or a halide, or a molecular group such as a methyl group. Such a derivative may be prepared by any method known to those of skill in the art. The properties of such derivatives may be assayed for their desired properties by any means known to those of skill in the art. As used herein, "analogs" include structural equivalents or mimetics.

The solution agent used in the solution can be aqueous such as water, one or more organic solvents, or a combination thereof. When used, the organic solvents can be water miscible or non-water miscible. Suitable organic solvents include but are not limited to ethanol, methanol, tetrahydrofuran, acetonitrile, acetone, tert-butyl alcohol, dimethyl sulfoxide, N,N-dimethyl formamide, diethyl ether, methylene chloride, ethyl acetate, isopropyl acetate, butyl acetate, propyl acetate, toluene, hexanes, heptane, pentane, and combinations thereof.

By "immediate release" is meant a release of an API to an environment over a period of seconds to no more than about 30 minutes once release has begun and release begins within no more than about 2 minutes after administration. An immediate release does not exhibit a significant delay in the release of drug.

By "rapid release" is meant a release of an API to an environment over a period of 1-59 minutes or 0.1 minute to three hours once release has begun and release can begin within a few minutes after administration or after expiration of a delay period (lag time) after administration.

As used herein, the term "extended release" profile assumes the definition as widely recognized in the art of pharmaceutical sciences. An extended release dosage form will release an API at a substantially constant rate over an extended period of time or a substantially constant amount of API will be released incrementally over an extended period of time. An extended release tablet generally effects at least a two-fold reduction in dosing frequency as compared to the API presented in a conventional dosage form (e.g., a solution or rapid releasing conventional solid dosage forms).

By "controlled release" is meant a release of an API to an environment over a period of about eight hours up to about 12 hours, 16 hours, 18 hours, 20 hours, a day, or more than a day. By "sustained release" is meant an extended release of an active agent to maintain a constant drug level in the blood or target tissue of a subject to which the device is administered.

The term "controlled release", as regards to drug release, includes the terms "extended release," "prolonged release," "sustained release," or "slow release," as these terms are used in the pharmaceutical sciences. A controlled release can begin within a few minutes after administration or after expiration of a delay period (lag time) after administration.

A "slow release dosage form" is one that provides a slow rate of release of API so that API is released slowly and approximately continuously over a period of 3 hours, 6 hours, 12 hours, 18 hours, a day, 2 or more days, a week, or 2 or more weeks, for example.

The term "mixed release" as used herein refers to a pharmaceutical agent that includes two or more release profiles for one or more active pharmaceutical ingredients. For example, the mixed release may include an immediate release and an extended release portion, each of which may be the same API or each may be a different API.

A "timed release dosage form" is one that begins to release an API after a predetermined period of time as measured from the moment of initial exposure to the environment of use.

A "targeted release dosage form" generally refers to an oral dosage form that is designed to deliver an API to a particular portion of the gastrointestinal tract of a subject. An exemplary targeted dosage form is an enteric dosage form that delivers a drug into the middle to lower intestinal tract but not into the stomach or mouth of the subject. Other targeted dosage forms can deliver to other sections of the gastrointestinal tract such as the stomach, jejunum, ileum, duodenum, cecum, large intestine, small intestine, colon, or rectum.

By "delayed release" is meant that initial release of an API occurs after expiration of an approximate delay (or lag) period. For example, if release of an API from an extended release composition is delayed two hours, then release of the API begins at about two hours after administration of the composition, or dosage form, to a subject. In general, a delayed release is opposite of an immediate release, wherein release of an API begins after no more than a few minutes after administration. Accordingly, the API release profile from a particular composition can be a delayed-extended release or a delayed-rapid release. A "delayed-extended" release profile is one wherein extended release of an API begins after expiration of an initial delay period. A "delayed-rapid" release profile is one wherein rapid release of an API begins after expiration of an initial delay period.

A "pulsatile release dosage form" is one that provides pulses of high API concentration, interspersed with low concentration troughs. A pulsatile profile containing two peaks may be described as "bimodal." A pulsatile profile of more than two peaks may be described as multi-modal.

A "pseudo-first order release profile" is one that approximates a first order release profile. A first order release profile characterizes the release profile of a dosage form that releases a constant percentage of an initial API charge per unit time.

A "pseudo-zero order release profile" is one that approximates a zero-order release profile. A zero-order release profile characterizes the release profile of a dosage form that releases a constant amount of API per unit time.

II. Thermokinetic Compounding

In certain embodiments, the pharmaceutical formulations of the present disclosure are processed in a thermokinetic chamber as disclosed in U.S. Pat. No. 8,486,423, which is incorporated herein by reference. This disclosure is directed to a method of blending certain heat sensitive or thermolabile components in a thermokinetic mixer by using multiple speeds during a single, rotationally continuous operation on a batch containing thermolabile components in order to minimize any substantial thermal degradation, so that the resulting pharmaceutical compositions have increased bioavailability and stability.

In a TKC chamber the average temperature inside the chamber is ramped up to a pre-defined final temperature over the duration of processing to achieve thermokinetic compounding of an API and the one or more pharmaceutically acceptable excipients, adjuvants, additional APIs, or combinations thereof, into a composite. The length of processing and exposure to elevated temperatures during thermokinetic compounding will generally be below the thermal sensitivity threshold of the API, the excipients, the adjuvants, the additional APIs, or all of these. Multiple speeds may be used during a single, rotationally continuous TKC operation to achieve optimal thermokinetic mixing of the API and the one or more pharmaceutically acceptable excipients, adjuvants and additional APIs, or combinations thereof, into a composite with minimal thermal degradation. The pre-defined final temperature and speed(s) are selected to reduce the possibility that the API, excipients, adjuvants, additional APIs and/or processing agents are degraded or their functionality is impaired during processing. Generally, the pre-defined final temperature, pressure, time of processing and other environmental conditions (e.g., pH, moisture, buffers, ionic strength, $O_2$) will be selected to substantially eliminate API, excipient, adjuvant, additional APIs and/or processing agent degradation.

Other embodiments include:
producing solid dispersions of DFX, with or without additional APIs, by processing at low temperatures for very brief durations;
producing solid dispersions of DFX, with or without additional APIs, in thermolabile polymers and excipients by processing at low temperatures for very brief durations;
rendering DFX, with or without additional APIs, amorphous while dispersing in a polymeric, non-polymeric, or combination excipient carrier system;
rendering DFX, with or without additional APIs, amorphous while dispersing in a polymeric, non-polymeric, or combination excipient carrier system and adjuvants;
producing composites comprising DFX, with or without additional APIs, and one or more thermolabile polymers without the use of processing agents; and Additionally, compositions of the present disclosure may be processed using any technique known to one skilled in the art to produce a solid formulation, including fusion or solvent based techniques. Specific examples of these techniques include extrusion, melt extrusion, hot-melt extrusion, spray congealing, spray drying, hot-spin mixing, ultrasonic compaction, and electrostatic spinning.

III. Deferasirox

A. Background

Deferasirox (DFX) is an orally active iron (as $Fe^{3+}$) chelating agent indicated for the treatment of chronic iron overload. It is a tridentate ligand that binds iron with high affinity in a 2:1 ratio. The molecular structure of DFX is provided in below:

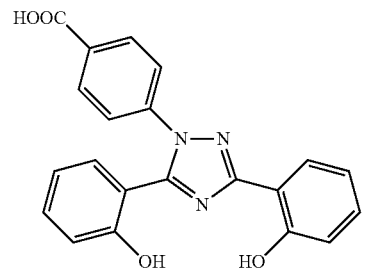 [SMILES: O=C(O)c1ccc(-n2nc(-c3ccccc3O)nc2-c2ccccc2O)cc1]

Its molecular formula is $C_{21}H_{15}N_3O_4$ with a corresponding molecular weight of 373.4 g/mol. The melting point of DFX is 264-265° C. and it has a Log P value of 6.3 (Merck Index). It has pKa values of 4.57, 8.71, and 10.56 indicating compound is weakly acidic[1]. DFX exhibits pH dependent solubility: it is insoluble in acidic media and is increasingly more soluble with increasing pH[1]. The reported water solubility of DFX is 0.4 mg/ml at 25° C.[1].

As stated above, the pharmacokinetics of orally administered DFX can be characterized as highly variable with the most probable source of variability being its pH-dependent solubility. Weakly acidic compounds with low solubility in gastric fluid have a tendency to form insoluble aggregated structures when exposed to acidic media for extended durations absent the proper delivery system[2]. When these insoluble structures are formed in the stomach, dissolution and absorption of the compound from the intestinal lumen is substantially reduced despite relatively good solubility of the free compound in intestinal fluids. As gastrointestinal pH can vary widely for a given individual from day-to-day and between individuals based on nutritional and diseased states and/or the influence of medications, it is understood that the solubility properties of DFX can lead to erratic oral absorption, and consequently, diminished therapeutic outcomes.

The absolute bioavailability of DFX tablets for oral suspension (Exjade®) has been reported to be 70% compared to an intravenous dose (see Exjade® package insert). However, it has also been reported that a significant proportion of transfusional iron overload patients are poor responders to DFX, which was directly correlated to low systemic exposure in a recent clinical study[3]. Further, substantial positive food effect has been reported for DFX, with iron overload patients exhibiting two-fold higher exposure when DFX is administered with a high fat meal. At steady state (7-day dosing), 84% of the total DFX dose was recovered in the feces as unchanged drug, which was partly attributable to incomplete intestinal absorption[4]. These clinical findings suggest that an improved oral delivery system for DFX could improve therapeutic outcomes by: (1) reducing intra and inter-patient variability, (2) improving absorption/enabling therapy for non-responders, and (3) eliminating food effects. Finally, reducing the therapeutic dose via bioavailability enhancement and mitigating variability could also lead to a reduction in the frequency of adverse events associated with DFX toxicity.

B. Iron Toxicity

Iron overload, also known as hemochromatosis, indicates accumulation of iron in the body from any cause. The most important causes are hereditary hemochromatosis (HHC), a genetic disorder, and transfusional iron overload, which can result from repeated blood transfusion.

1. Signs and Symptoms

Organs commonly affected by hemochromatosis are the liver, heart, and endocrine glands. Haemochromatosis may present with the following clinical syndromes:
Cirrhosis of the liver (varies from zonal iron deposition to fibrosis)
Diabetes due to selective iron deposition in pancreatic islet beta cells leading to functional failure and cell death
Cardiomyopathy
Arthritis (calcium pyrophosphate deposition in joints)
Testicular failure
Slate grey discoloration of the skin
Joint pain and bone pain 2. Development The causes can be distinguished between primary cases (hereditary or genetically determined) and less frequent secondary cases (acquired during life). People of Celtic (Irish, Scottish, Welsh, Cornish, Breton, etc.), British, and Scandinavian origin have a particularly high incidence of whom about 10% are carriers of the C282Y mutation on the HFE gene associated with HLA-A3 and 1% suffer from the condition.

Primary Hemochromatosis.

Although it was known for most of the 20th century that most cases of hemochromatosis were inherited, they were incorrectly assumed to depend on a single gene. The overwhelming majority actually depend on mutations of the HFE gene discovered in 1996, but since then others have been discovered and sometimes are grouped together as "non-classical hereditary hemochromatosis," "non-HFE related hereditary hemochromatosis" or "non-HFE hemochromatosis." Most types of hereditary hemochromatosis have autosomal recessive inheritance, while type 4 has autosomal dominant inheritance.

Secondary Hemochromatosis.

Severe chronic hemolysis of any cause, including intravascular hemolysis and ineffective erythropoiesis (hemolysis within the bone marrow) Multiple frequent blood transfusions (either whole blood or just red blood cells), which are usually needed either by individuals with hereditary anemias (such as β-thalassaemia major, sickle cell anemia, and Diamond-Blackfan anemia) or by older patients with severe acquired anemias such as in myelodysplastic syndromes. Excess parenteral iron supplements, such as what can acutely happen in iron poisoning.

Some disorders do not normally cause hemochromatosis on their own, but may do so in the presence of other predisposing factors. These include cirrhosis (especially related to alcohol abuse), steatohepatitis of any cause, porphyria cutanea tarda, prolonged hemodialysis, and post-portacaval shunting 3. Detection There are several methods available for diagnosing and monitoring iron loading including serum ferritin, liver biopsy, HFE and MRI. Serum ferritin testing is a low-cost, readily available, and minimally invasive method for assessing body iron stores. However, the major problem with using it as an indicator of iron overload is that it can be elevated in a range of other medical conditions unrelated to iron levels including infection, inflammation, fever, liver disease, renal disease, and cancer. Also, total iron binding capacity may be low, but can also be normal.

Positive HFE analysis confirms the clinical diagnosis of hemochromatosis in asymptomatic individuals with blood tests showing increased iron stores, or for predictive testing of individuals with a family history of hemochromatosis. The alleles evaluated by HFE gene analysis are evident in ~80% of patients with hemochromatosis; a negative report for HFE gene does not rule out hemochromatosis. In a patient with negative HFE gene testing, elevated iron status for no other obvious reason, and family history of liver disease, additional evaluation of liver iron concentration is indicated. In this case, diagnosis of hemochromatosis is based on biochemical analysis and histologic examination of a liver biopsy. Assessment of the hepatic iron index (HII) is considered the "gold standard" for diagnosis of hemochromatosis. Magnetic resonance imaging (MRI) is emerging as a noninvasive alternative to accurately estimate iron deposition levels in the liver as well as heart, joints, and pituitary gland.

Family members of those with primary hemochromatosis should be screened to determine if they are a carrier or if they could develop the disease. This can allow preventive measures to be taken. Screening the general population is not recommended.

4. Treatment

Routine treatment in an otherwise-healthy person consists of regularly scheduled phlebotomies (bloodletting). When first diagnosed, the phlebotomies may be fairly frequent, perhaps as often as once a week, until iron levels can be brought to within normal range. Once iron and other markers are within the normal range, phlebotomies may be scheduled every other month or every three months depending upon the patient's rate of iron loading. Each session typically draws from 450 to 500 cc.

For those unable to tolerate routine blood draws, there is a chelating agent available for use. The drug deferoxamine binds with iron in the bloodstream and enhances its elimination via urine and feces. Typical treatment for chronic iron overload requires subcutaneous injection over a period of 8-12 hours daily. Two newer iron chelating drugs that are licensed for use in patients receiving regular blood transfusions to treat thalassaemia (and, thus, who develop iron overload as a result) are deferasirox and deferiprone.

5. Prognosis

A third of those untreated develop hepatocellular carcinoma. Affected individuals over age 40 or who have high serum ferritin levels are at risk for developing cirrhosis.

Significant problems occur in around one in ten.

C. Delivery

A variety of administration routes are available for delivering DFX to a patient in need. The particular route selected will depend upon the particular drug selected, the weight and age of the patient, and the dosage required for therapeutic effect. The pharmaceutical compositions may conveniently be presented in unit dosage form. DFX suitable for use in accordance with the present disclosure, and its pharmaceutically acceptable salts, derivatives, analogs, prodrugs, and solvates thereof, can be administered alone, but will generally be administered in admixture with a suitable pharmaceutical excipient, adjuvant, diluent, or carrier selected with regard to the intended route of administration and standard pharmaceutical practice, and can in certain instances be administered with one or more additional API(s), preferably in the same unit dosage form.

DFX may be used in a variety of application modalities, including oral delivery as tablets, capsules or suspensions; pulmonary and nasal delivery; topical delivery as emulsions, ointments or creams; transdermal delivery; and parenteral delivery as suspensions, microemulsions or depot. As used herein, the term "parenteral" includes subcutaneous, intravenous, intramuscular, or infusion routes of administration.

D. Excipients

The excipients and adjuvants that may be used in the presently disclosed compositions and composites, while potentially having some activity in their own right, for example, antioxidants, are generally defined for this application as compounds that enhance the efficiency and/or efficacy of DFX. It is also possible to have more than one API in a given solution, so that the particles formed contain more than one API.

Any pharmaceutically acceptable excipient known to those of skill in the art may be used to produce the composites and compositions disclosed herein. Examples of excipients for use with the present disclosure include, but are not limited to, e.g., a pharmaceutically acceptable polymer, a thermolabile polymeric excipient, or a non-polymeric excipient. Other non-limiting examples of excipients include, lactose, glucose, starch, calcium carbonate, kaoline, crystalline cellulose, silicic acid, water, simple syrup, glucose solution, starch solution, gelatin solution, carboxymethyl cellulose, shellac, methyl cellulose, polyvinyl pyrrolidone, dried starch, sodium alginate, powdered agar, calcium carmelose, a mixture of starch and lactose, sucrose, butter, hydrogenated oil, a mixture of a quaternary ammonium base and sodium lauryl sulfate, glycerine and starch, lactose, bentonite, colloidal silicic acid, talc, stearates, and polyethylene glycol, sorbitan esters, polyoxyethylene sorbitan fatty acid esters, polyoxyethylene alkyl ethers, poloxamers (polyethylene-polypropylene glycol block copolymers), sucrose esters, sodium lauryl sulfate, oleic acid, lauric acid, vitamin E TPGS, polyoxyethylated glycolysed glycerides, dipalmitoyl phosphadityl choline, glycolic acid and salts, deoxycholic acid and salts, sodium fusidate, cyclodextrins, polyethylene glycols, polyglycolyzed glycerides, polyvinyl alcohols, polyacrylates, polymethacrylates, polyvinylpyrrolidones, phosphatidyl choline derivatives, cellulose derivatives, biocompatible polymers selected from poly (lactides), poly(glycolides), poly(lactide-co-glycolides), poly(lactic acid)s, poly(glycolic acid)s, poly(lactic acid-co-glycolic acid)s and blends, combinations, and copolymers thereof.

As stated, excipients and adjuvants may be used to enhance the efficacy and efficiency of the API. Additional non-limiting examples of compounds that can be included are binders, carriers, cryoprotectants, lyoprotectants, surfactants, fillers, stabilizers, polymers, protease inhibitors, antioxidants, bioavailability enhancers and absorption enhancers. The excipients may be chosen to modify the intended function of the active ingredient by improving flow, or bio-availability, or to control or delay the release of the API. Specific nonlimiting examples include: sucrose, trehaolose, Span 80, Span 20, Tween 80, Brij 35, Brij 98, Pluronic, sucroester 7, sucroester 11, sucroester 15, sodium lauryl sulfate (SLS, sodium dodecyl sulfate. SDS), dioctyl sodium sulphosuccinate (DSS, DOSS, dioctyl docusate sodium), oleic acid, laureth-9, laureth-8, lauric acid, vitamin E TPGS, Cremophor® EL, Cremophor® RH, Gelucire® 50/13, Gelucire® 53/10, Gelucire® 44/14, Labrafil®, Solutol® HS, dipalmitoyl phosphadityl choline, glycolic acid and salts, deoxycholic acid and salts, sodium fusidate, cyclodextrins, polyethylene glycols, Labrasol®, polyvinyl alcohols, polyvinyl pyrrolidones and tyloxapol. Using the process of the present disclosure, the morphology of the active ingredients can be modified, resulting in highly porous microparticles and nanoparticles.

Exemplary polymer carriers or thermal binders that may be used in the presently disclosed compositions and composites include but are not limited to polyethylene oxide; polypropylene oxide; polyvinylpyrrolidone; polyvinylpyrrolidone-co-vinylacetate; acrylate and methacrylate copolymers; polyethylene; polycaprolactone; polyethylene-co-polypropylene; alkylcelluloses such as methylcellulose; hydroxyalkylcelluloses such as hydroxymethylcellulose, hydroxyethylcellulose, hydroxypropylcellulose, and hydroxybutylcellulose; hydroxyalkyl alkylcelluloses such as hydroxyethyl methylcellulose and hydroxypropyl methylcellulose; starches, pectins; polysaccharides such as tragacanth, gum arabic, guar gum, and xanthan gum. One embodiment of the binder is poly(ethylene oxide) (PEO), which can be purchased commercially from companies such as the Dow Chemical Company, which markets PEO under the POLY OX® exemplary grades of which can include WSR N80 having an average molecular weight of about 200,000; 1,000,000; and 2,000,000.

Suitable polymer carriers or thermal binders that may or may not require a plasticizer include, for example, Eudragit® RS PO, Eudragit® S100, Kollidon® SR (poly (vinyl acetate)-co-poly(vinylpyrrolidone) copolymer), Ethocel® (ethylcellulose), HPC (hydroxypropylcellulose), cellulose acetate butyrate, poly(vinylpyrrolidone) (PVP), poly (ethylene glycol) (PEG), poly(ethylene oxide) (PEO), poly (vinyl alcohol) (PVA), hydroxypropyl methylcellulose (HPMC), ethylcellulose (EC), hydroxyethylcellulose (HEC), sodium carboxymethyl-cellulose (CMC), dimethylaminoethyl methacrylate-methacrylic acid ester copolymer, ethylacrylate-methylmethacrylate copolymer (GA-MMA), C-5 or 60 SH-50 (Shin-Etsu Chemical Corp.), cellulose acetate phthalate (CAP), cellulose acetate trimelletate (CAT), poly(vinyl acetate) phthalate (PVAP), hydroxypropylmethylcellulose phthalate (HPMCP), poly(methacrylate ethylacrylate) (1:1) copolymer (MA-EA), poly(methacrylate methylmethacrylate) (1:1) copolymer (MA-MMA), poly (methacrylate methylmethacrylate) (1:2) copylymer, Eudragit® L-30-D (MA-EA, 1:1), Eudragit® L100-55 (MA-EA, 1:1), Eudragit® EPO (poly(butyl methacylate-co-(2-dimethylaminoethyl) methacrylate-co-methyl methacrylate) 1:2:1), hydroxypropylmethylcellulose acetate succinate (HPMCAS), Coateric® (PVAP), Aquateric® (CAP), and AQUACOAT® (HPMCAS), Soluplus® (polyvinyl caprolactam-polyvinyl acetate-polyethylene glycol graft copolymer, BASF), Luvitec® K 30 (polyvinylpyrrolidone, PVP), Kollidon® (polyvinylpyrrolidone, PVP), polycaprolactone, starches, pectins; polysaccharides such as tragacanth, gum arabic, guar gum, and xanthan gum.

The carrier may also contain various functional excipients, such as: hydrophilic polymer, antioxidant, super-disintegrant, surfactant including amphiphilic molecules, wetting agent, stabilizing agent, retardant, similar functional excipient, or combination thereof, and plasticizers including citrate esters, polyethylene glycols, PG, triacetin, diethylphthalate, castor oil, and others known to those or ordinary skill in the art. Extruded material may also include an acidifying agent, adsorbent, alkalizing agent, buffering agent, colorant, flavorant, sweetening agent, diluent, opaquant, complexing agent, fragrance, preservative or a combination thereof.

Exemplary hydrophilic polymers which can be a primary or secondary polymeric carrier that can be included in the composites or composition disclosed herein include poly (vinyl alcohol) (PVA), polyethylene-polypropylene glycol (e.g., POLOXAMER®), carbomer, polycarbophil, or chitosan. Hydrophilic polymers for use with the present disclosure may also include one or more of hydroxypropyl methylcellulose, carboxymethylcellulose, hydroxypropyl cellulose, hydroxyethyl cellulose, methylcellulose, natural gums such as gum guar, gum acacia, gum tragacanth, or gum xanthan, and povidone. Hydrophilic polymers also include polyethylene oxide, sodium carboxymethycellulose, hydroxyethyl methyl cellulose, hydroxymethyl cellulose, carboxypolymethylene, polyethylene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), carrageenate alginates, carbomer, ammonium alginate, sodium alginate, or mixtures thereof.

Compositions with enhanced solubility may comprise a mixture of DFX and an additive that enhances the solubility of the DFX. Examples of such additives include but are not limited to surfactants, polymer carriers, pharmaceutical carriers, thermal binders or other excipients. A particular example may be a mixture of DFX with a surfactant or surfactants, DFX with a polymer or polymers, or DFX with a combination of a surfactant and polymer carrier or surfactants and polymer carriers. A further example is a composition where the DFX is a derivative or analog thereof.

Surfactants that can be used in the disclosed compositions to enhance solubility have been previously presented. Particular examples of such surfactants include but are not limited to sodium dodecyl sulfate, dioctyl docusate sodium, Tween 80, Span 20, Cremophor® EL or Vitamin E TPGS. Polymer carriers that can be used in the disclosed composition to enhance solubility have been previously presented. Particular examples of such polymer carriers include but are not limited to Soluplus®, Eudragit® L100-55, Eudragit® EPO, Kollidon® VA 64, Luvitec®. K 30, Kollidon®, AQOAT®-HF, and AQOAT®-LF. The composition of the present disclosure can thus be any combination of one or more of the APIs, zero, one or more of surfactants or zero, one or more of polymers presented herein.

Solubility can be indicated by peak solubility, which is the highest concentration reached of a species of interest over time during a solubility experiment conducted in a specified medium. The enhanced solubility can be represented as the ratio of peak solubility of the agent in a pharmaceutical composition of the present disclosure compared to peak solubility of the reference standard agent under the same conditions. Preferable, an aqueous buffer with a pH in the range of from about pH 4 to pH 8, about pH 5 to pH 8, about pH 6 to pH 7, about pH 6 to pH 8, or about pH 7 to pH 8, such as, for example, pH 4.0, 4.5, 5.0, 5.5, 6.0, 6.2, 6.4, 6.6, 6.7, 6.8, 6.9, 7.0, 7.1, 7.2, 7.4, 7.6, 7.8, or 8.0, may be used for determining peak solubility. This peak solubility ratio can be about 2:1, 3:1, 4:1, 5:1, 6:1, 7:1, 8:1, 9:1, 10:1, 12:1, 15:1, 20:1, 25:1, 30:1, 35:1, 40:1, 45:1, 50:1, 55:1 or higher.

Bioavailability can be indicated by the AUC of DFX as determined during in vivo testing, where AUC is the area under the blood concentration versus time curve for DFX. Enhanced bioavailability can be represented as the ratio of AUC of the DFX in a pharmaceutical composition of the present disclosure compared to AUC of the reference standard DFX under the same conditions. This AUC ratio reflecting enhanced bioavailability can be about 4:3, 5:3, 2:1, 5:1, 6:1, 7:1, 8:1, 9:1, 10:1, 12:1, 15:1, 20:1, 25:1, 30:1, 35:1, 40:1, 45:1, 50:1, 55:1, 60:1, 65:1, 70:1, 75:1, 80:1, 85:1, 90:1, 95:1, 98:1, 99:1, 100:1 or higher.

E. Other API's

In one embodiment, a second active pharmaceutical ingredient may be combined with DFX produced in accordance with the disclosed methods. Those of skill in the art are familiar with suitable tablet architectures (side-by-side tablets, layered tablets, coated tablets, etc.) to achieve a coformulation. The second active pharmaceutical ingredient may be a second iron chelator, an agent used in the treatment or prevention of osteoporosis, an anti-fungal agent, or an agent that increases the rate of production of red blood cells, such as amphotericin B, deferiprone, deferoxamine, erythropoietin, or risedronate.

IV. Examples

It will be understood that particular embodiments described herein are shown by way of illustration and not as limitations of the disclosure. The principal features of this disclosure can be employed in various embodiments without departing from the scope of the disclosure. All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

Example 1—KinetiSol® Processing of Various Deferasirox Compositions

KinetiSol® processing was performed with a cGMP TC-254B compounder designed by DisperSol Technologies.

Prior to compounding, DFX and excipients were accurately weighed and dispensed into a PE bag and hand-blended for 5 minutes. Blends were then manually charged into the KinetiSol® chamber for each trial. During processing, temperature, rotational speed, and motor amperage were continuously monitored up to the instantaneous discharge of the product upon achieving the set point temperature. Immediately following product ejection from the KinetiSol® compounder, the molten product mass was rapidly transferred to a pneumatic press where it was quenched at high pressure inside a 15 cm round stainless steel mold.

After quenching, each KinetiSol® product batch was milled using a L1A FitzMill® Comminutor (The Fitzpatrick Company, Elmhurst, Ill.) in hammer configuration fitted with a 0.020" screen at 6500-8000 RPM. The milled products were screened through a 60-mesh sieve (250 μm).

TABLE 1

Summary of amorphous DFX copositions produced by KinetiSol ®

| Lot number | Composition | Processing conditions Rotation speed [rpm], Ejection temperature [° C.] |
|---|---|---|
| 13-004-37 | 40% API, 60% Copovidone | 2400, 170 |
| 13-004-38 | 40% API, 60% Copovidone | 2400, 140 |
| 13-004-58 | 50% API, 50% Copovidone | 2400, 170 |
| 13-004-79 | 50% API, 50% Copovidone | 2400, 170 |
| 13-004-40 | 60% API, 40% Copovidone | 2400, 170 |
| 13-004-41 | 20% API, 80% HPMCAS L | 2400, 170 |
| 13-004-50 | 40% API, 60% Eudragit L100-55 | 3000 & 3400, 170 |
| 13-004-57 | 40% API, 30% Copovidone, 30% Eudragit L100-55 | 2900, 170 |
| 13-004-60 | 50% API, 25% Copovidone, 25% Eudragit L100-55 | 2900, 170 |
| 13-004-47 | 50% API, 33.3% Copovidone, 16.7% HPMCAS L | 2400, 170 |

Figure 1:
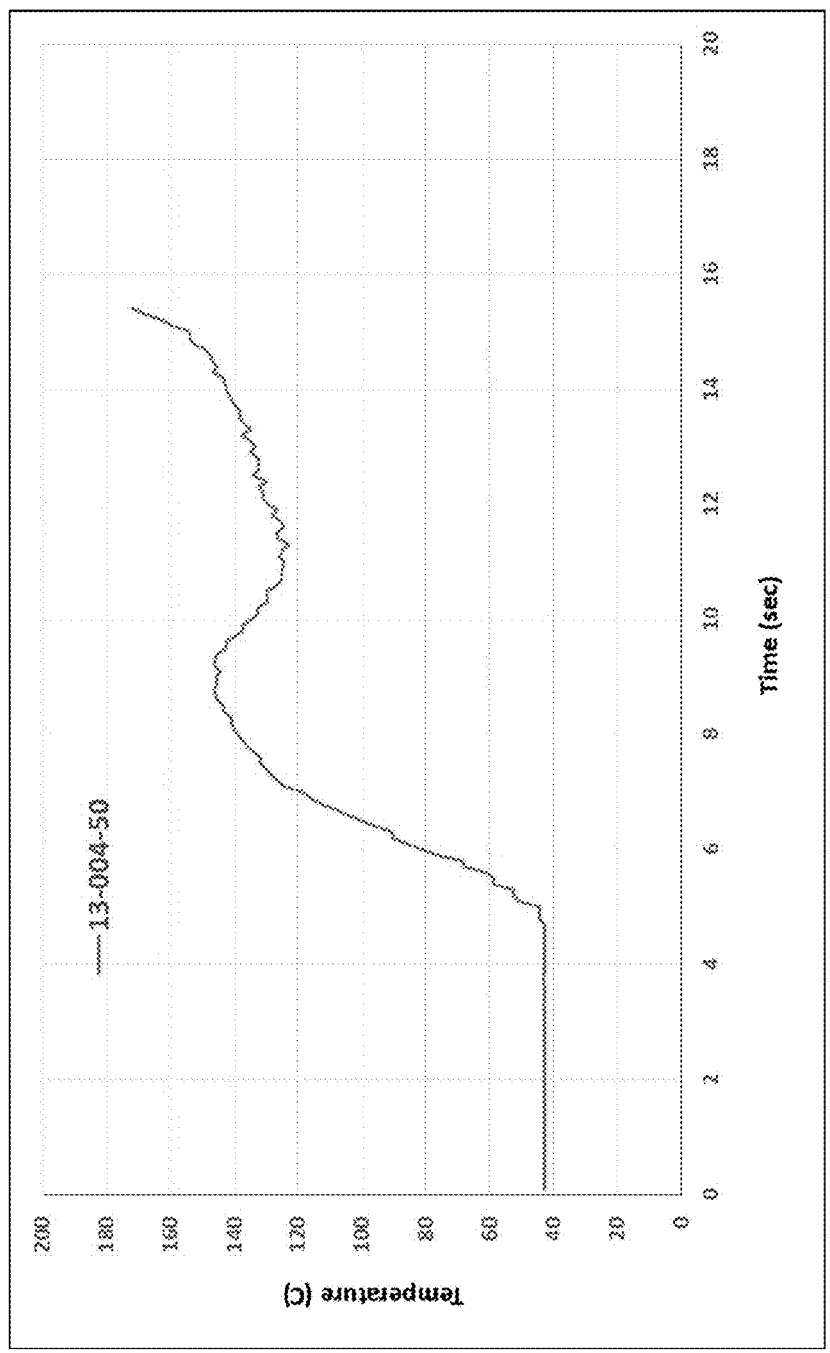
FIG. 1. KinetiSol® processing profile of lot 13-004-50 (40% DFX, 60% Eudragit L100-55).

FIG. 1 is a representative processing profile for an amorphous intermediate containing DFX and Eudragit L100-55. The profile demonstrates that the time for which the drug and polymer were exposed to elevated temperatures was limited to about 10 seconds and the maximum processing temperature was 170° C.; approximately 95° C. below the melting point of DFX. Producing an entirely amorphous DFX composition with high drug loading by thermal processing at temperatures well below the melting point and for very brief durations is a surprising result that is uniquely enabled by the KinetiSol® process. Furthermore, limiting the duration and extent of thermal exposure is critical to achieving product of this composition with acceptable drug and polymer purity.

Figure 2:
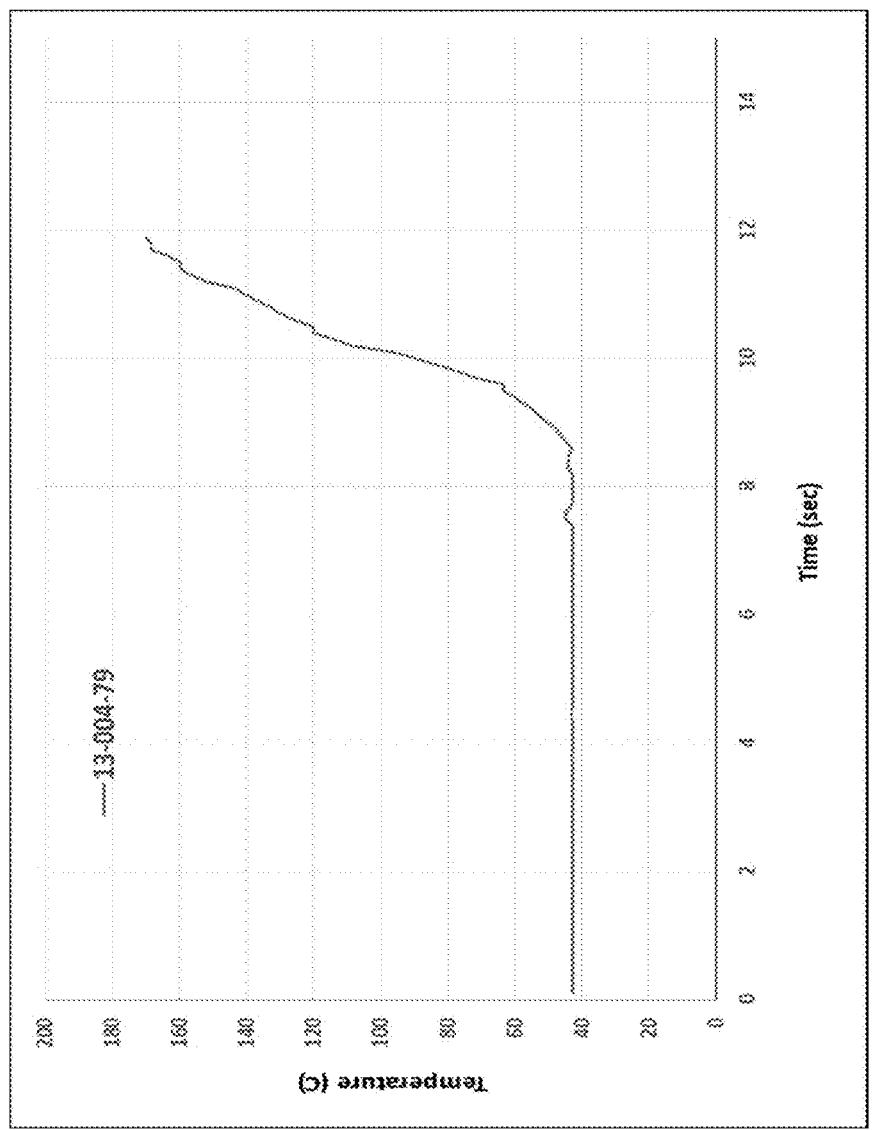
FIG. 2. KinetiSol® processing profile of lot 13-004-79 (50% API, 50% Copovidone).
Figure 3:
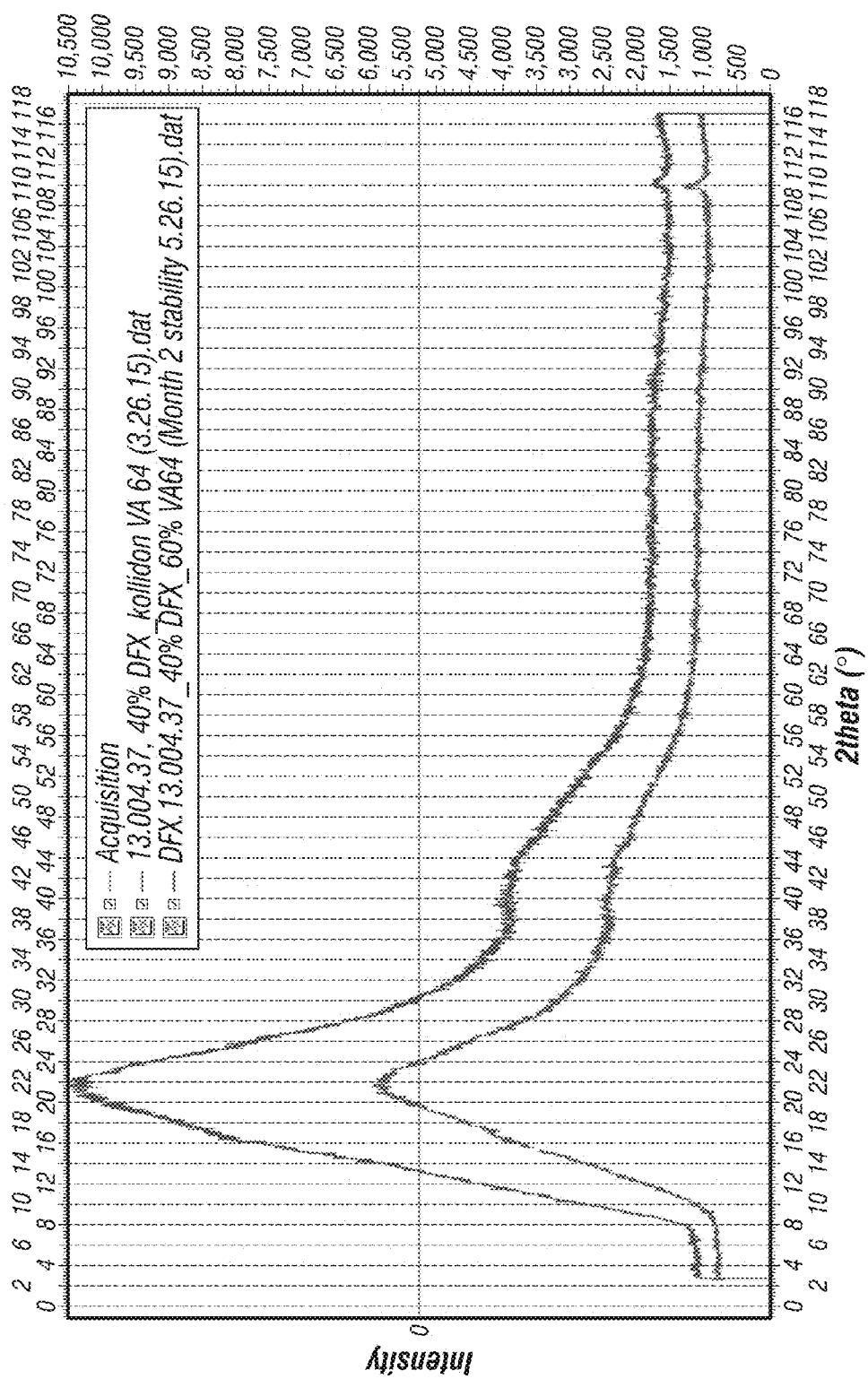
FIG. 3. XRD analysis of Lot 13-004-37 (40% DFX, 60% Copovidone). The red line represents the initial state of the product and the green line represents the product following 2 months storage at 40° C., 75% RH (open containers). The absence of peaks corresponding to crystalline DFX demonstrates that the drug was substantially amorphous in the formulation at both conditions.
Figure 4:
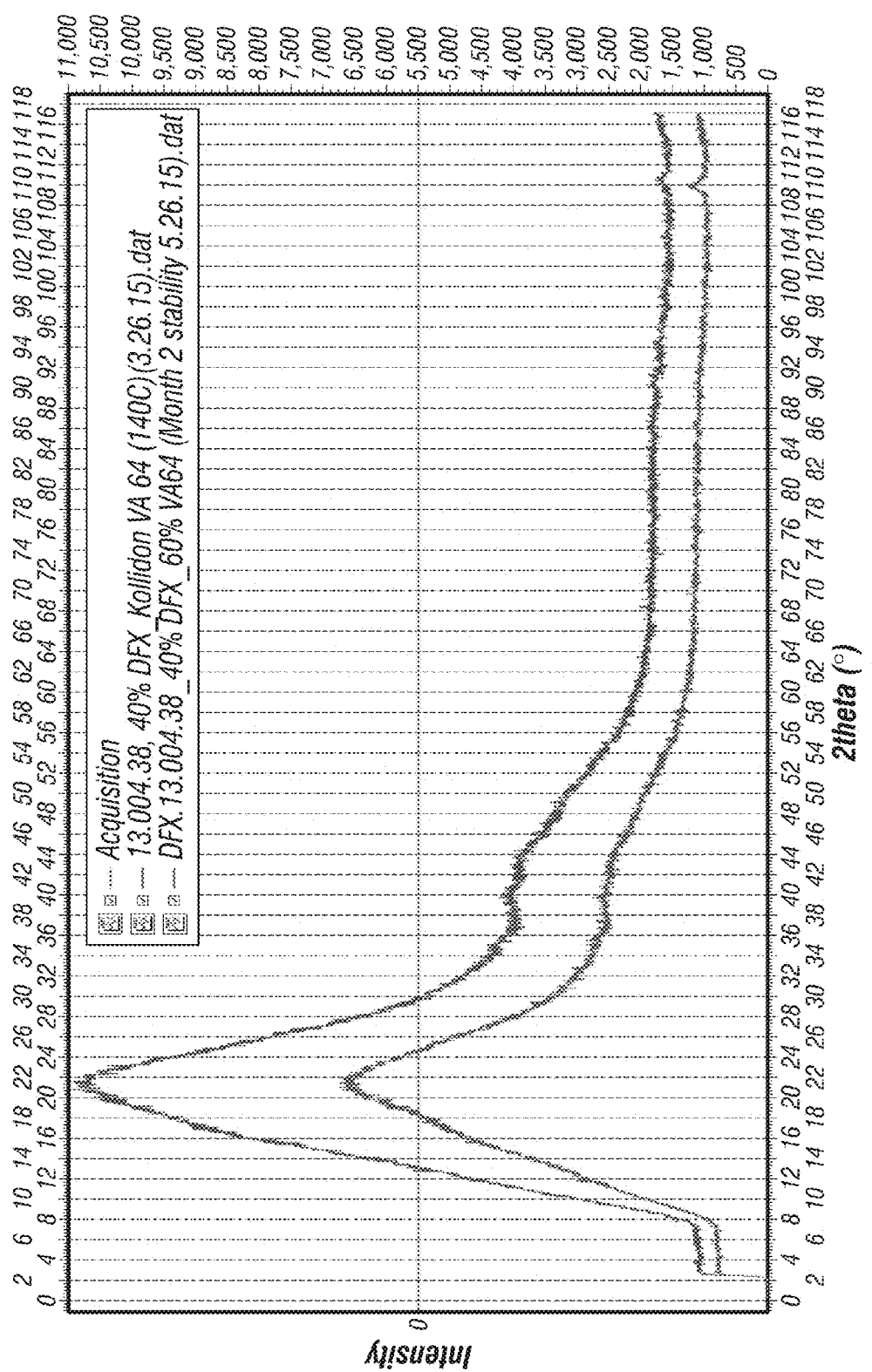
FIG. 4. XRD analysis of Lot 13-004-38 (40% DFX, 60% Copovidone). The red line represents the initial state of the product and the green line represents the product following 2 months storage at 40° C., 75% RH (open containers). The absence of peaks corresponding to crystalline DFX demonstrates that the drug was substantially amorphous in the formulation at both conditions.
Figure 5:
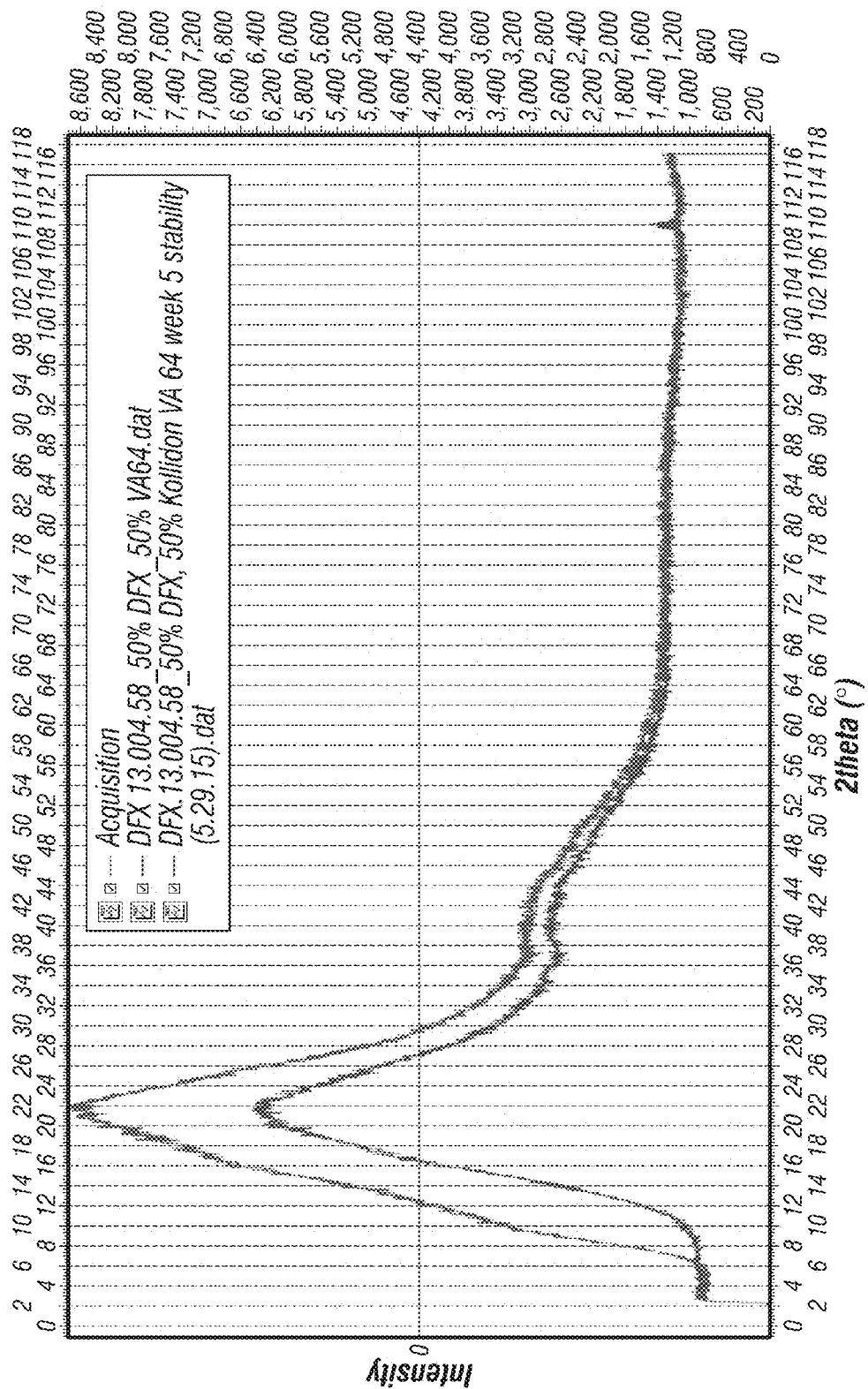
FIG. 5. XRD analysis of Lot 13-004-58 (50% DFX, 50% Copovidone). The red line represents the initial state of the product and the green line represents the product following 5 weeks storage at 40° C., 75% RH (open containers). The absence of peaks corresponding to crystalline DFX demonstrates that the drug was substantially amorphous in the formulation at both conditions.
Figure 6:
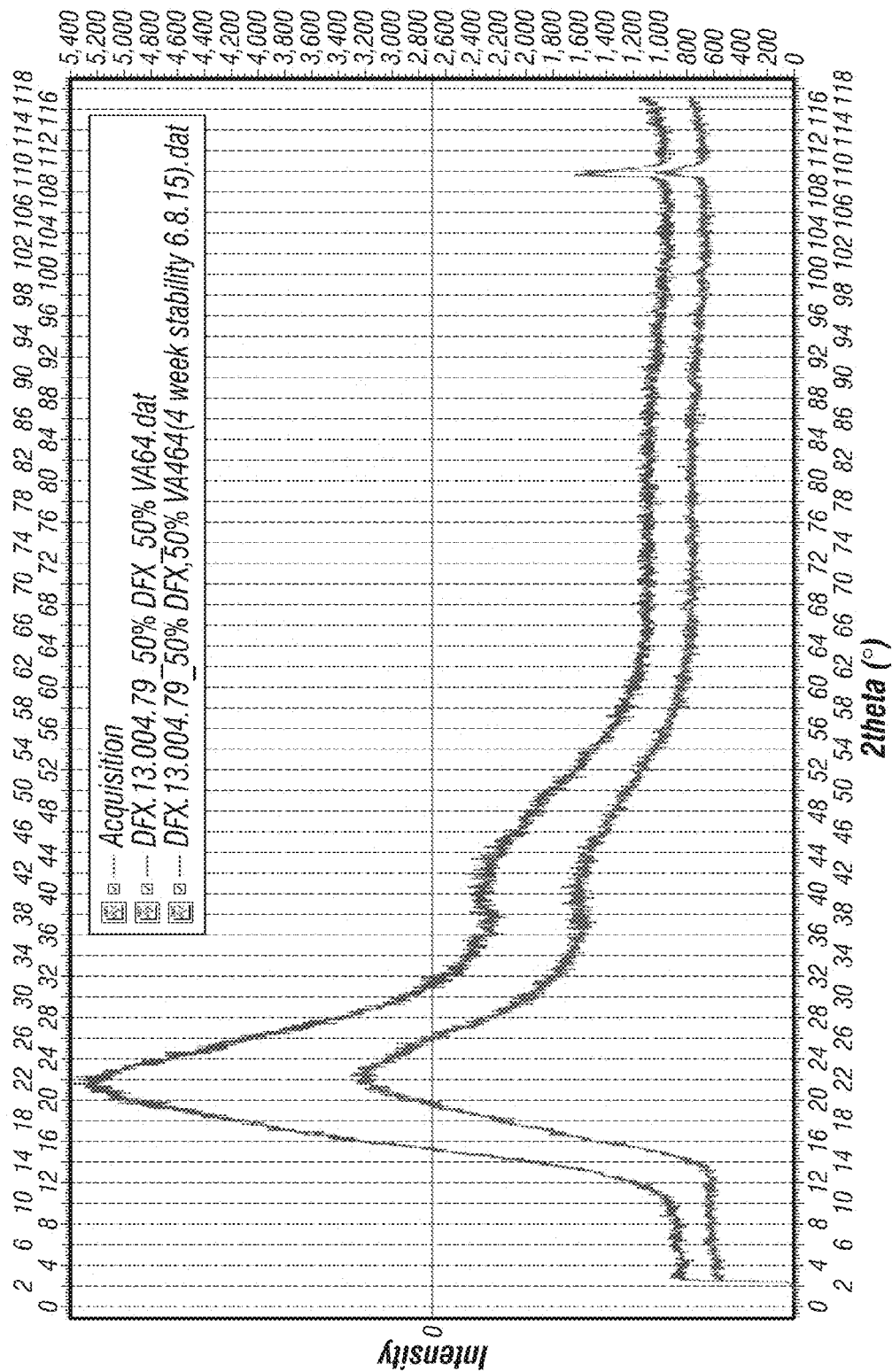
FIG. 6. XRD analysis of Lot 13-004-79 (50% DFX, 50% Copovidone). The red line represents the initial state of the product and the green line represents the product following 4 weeks storage at 40° C., 75% RH (open containers). The absence of peaks corresponding to crystalline DFX demonstrates that the drug was substantially amorphous in the formulation at both conditions.
Figure 7:
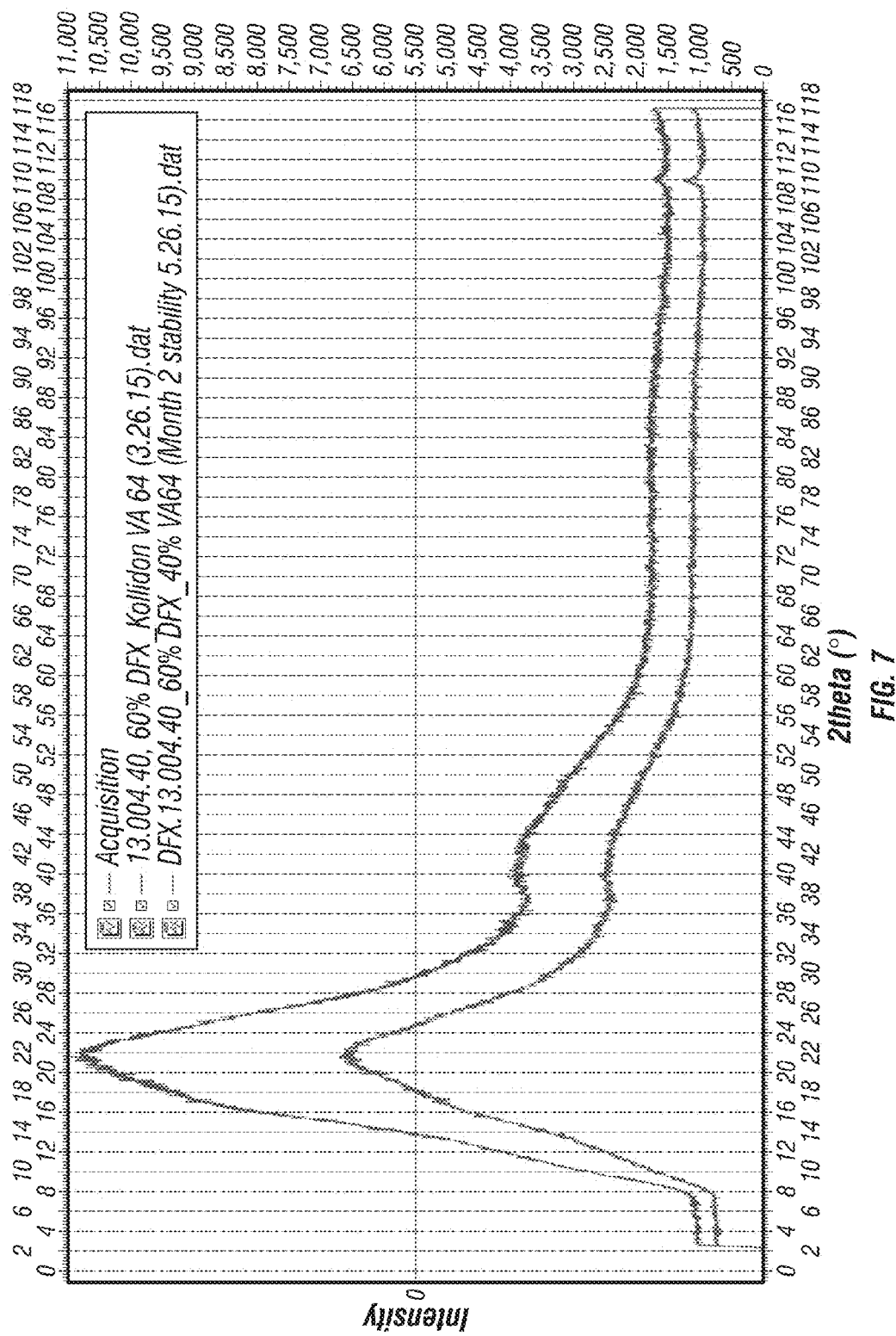
FIG. 7. XRD analysis of Lot 13-004-40 (60% DFX, 40% Copovidone). The red line represents the initial state of the product and the green line represents the product following 2 months storage at 40° C., 75% RH (open containers). The absence of peaks corresponding to crystalline DFX demonstrates that the drug was substantially amorphous in the formulation at both conditions.
Figure 8:
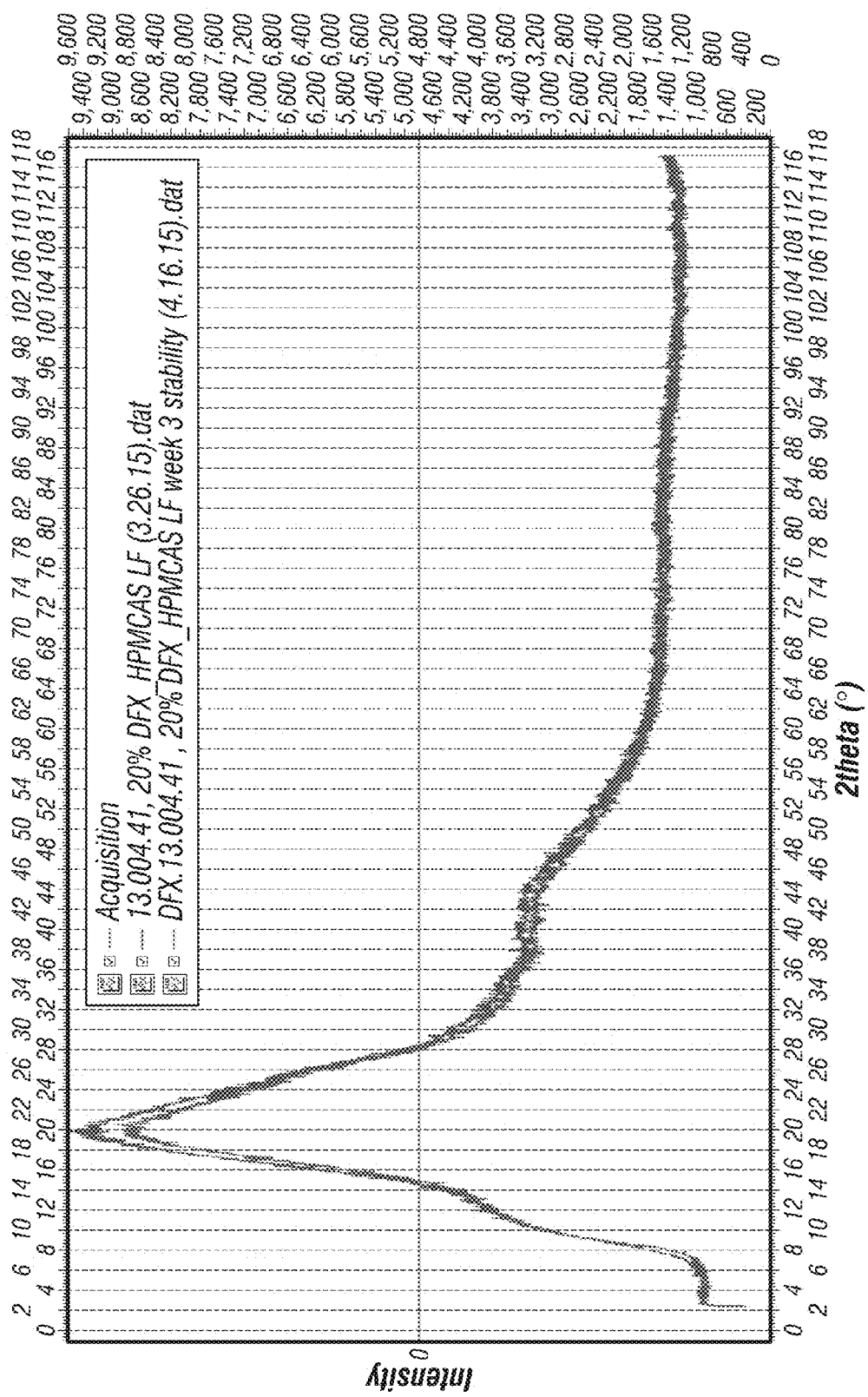
FIG. 8. XRD analysis of Lot 13-004-41 (20% DFX, 80% HPMCAS-LF). The red line represents the initial state of the product and the green line represents the product following 3 weeks storage at 40° C., 75% RH (open containers). The absence of peaks corresponding to crystalline DFX demonstrates that the drug was substantially amorphous in the formulation at both conditions.
Figure 9:
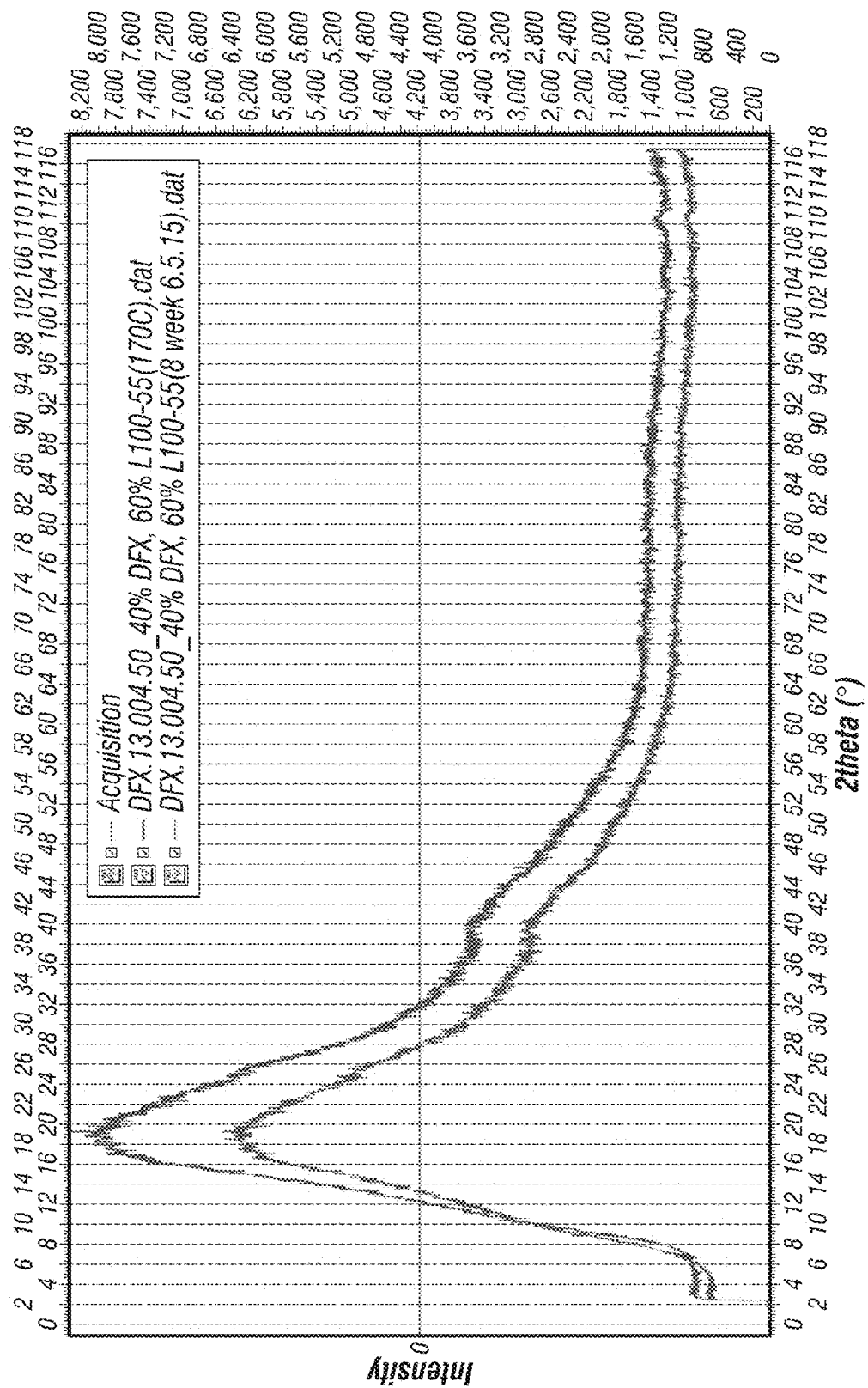
FIG. 9. XRD analysis of Lot 13-004-50 (40% DFX, 60% Eudragit L100-55). The red line represents the initial state of the product and the green line represents the product following 8 weeks storage at 40° C., 75% RH (open containers). The absence of peaks corresponding to crystalline DFX demonstrates that the drug was substantially amorphous in the formulation at both conditions.
Figure 10:
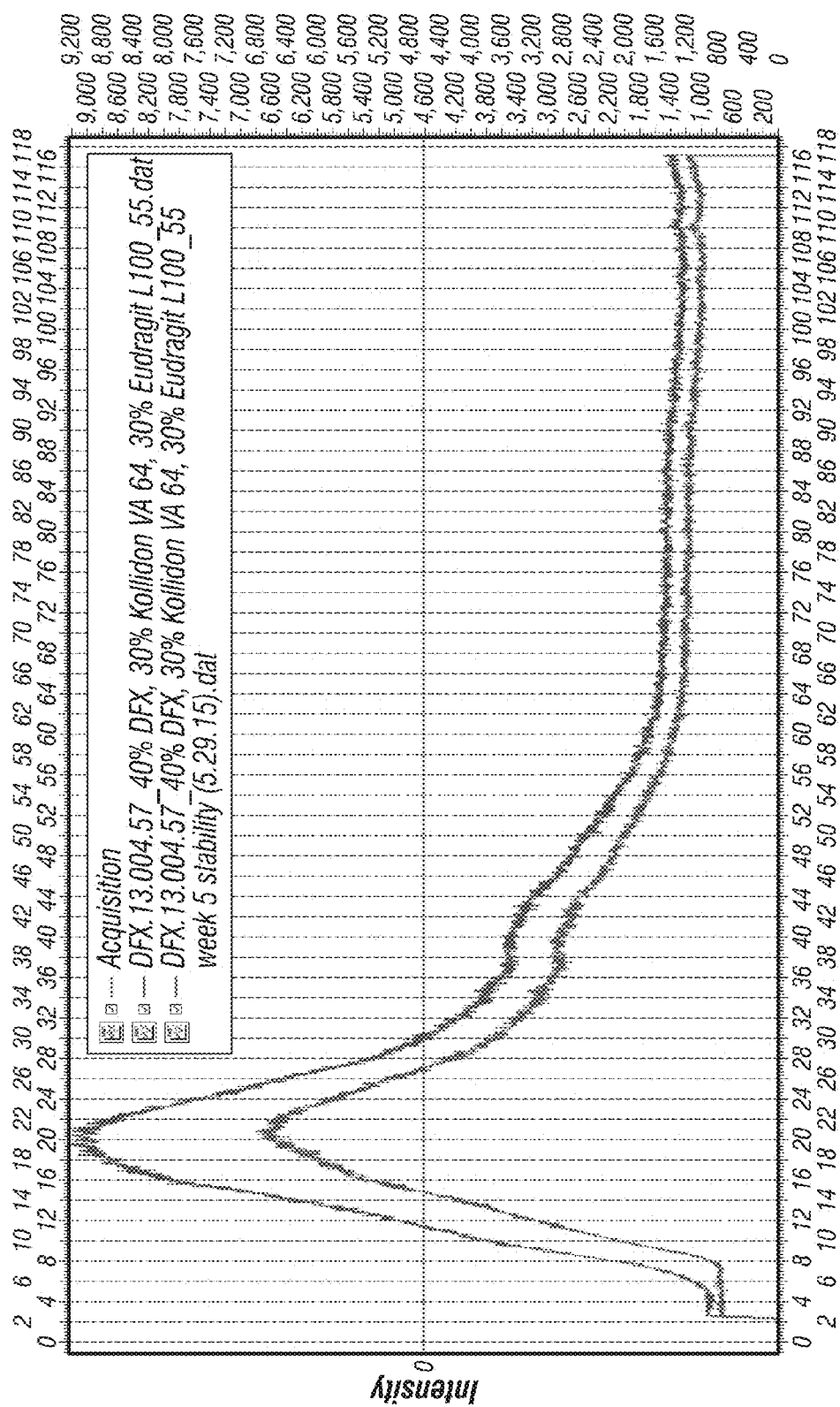
FIG. 10. XRD analysis of Lot 13-004-57 (40% DFX, 30% Eudragit L100-55, 30% Copovidone). The red line represents the initial state of the product and the green line represents the product following 5 weeks storage at 40° C., 75% RH (open containers). The absence of peaks corresponding to crystalline DFX demonstrates that the drug was substantially amorphous in the formulation at both conditions.
Figure 11:
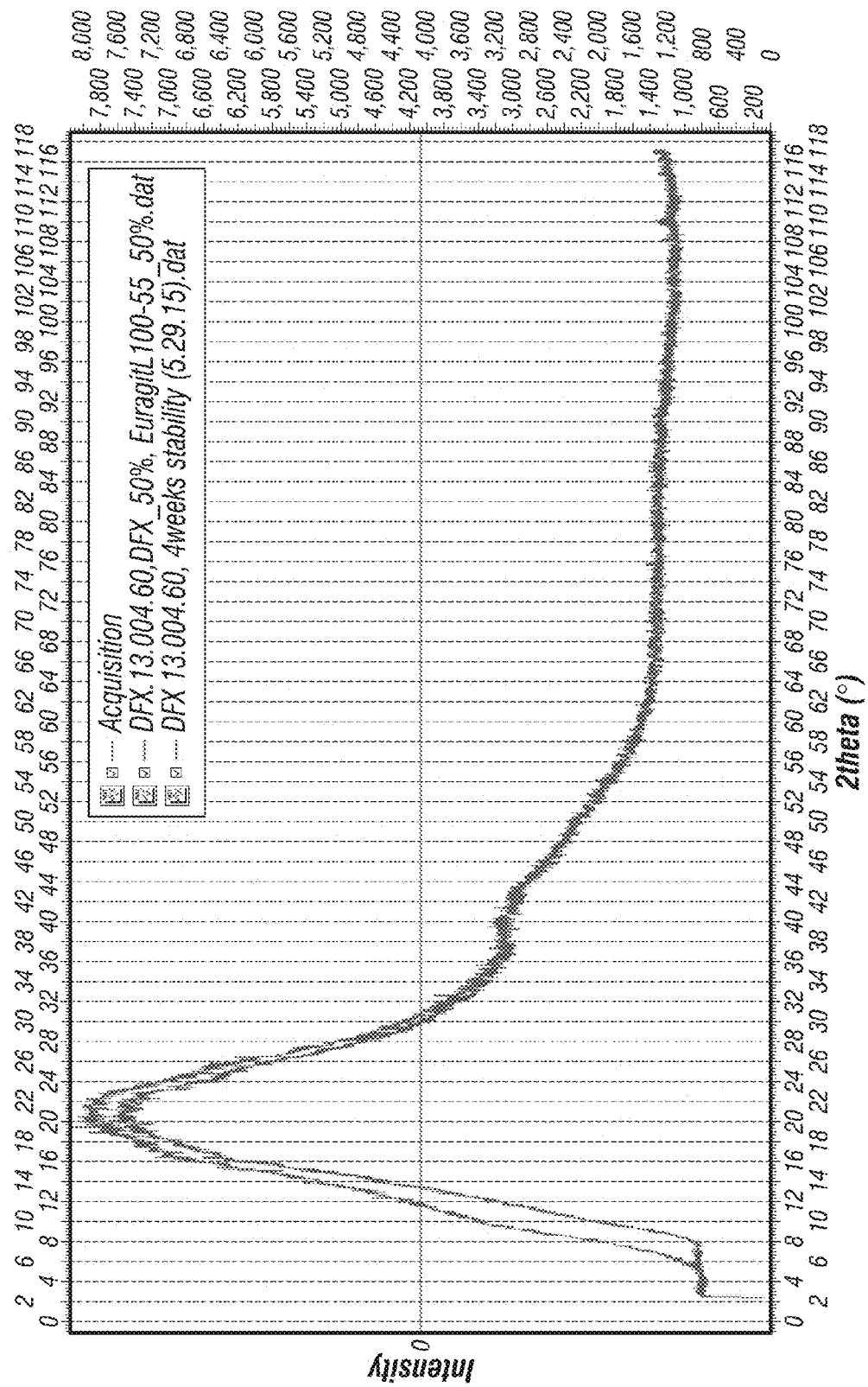
FIG. 11. XRD analysis of Lot 13-004-60 (50% DFX, 25% Eudragit L100-55, 25% Copovidone). The red line represents the initial state of the product and the green line represents the product following 4 weeks storage at 40° C., 75% RH (open containers). The absence of peaks corresponding to crystalline DFX demonstrates that the drug was substantially amorphous in the formulation at both conditions.
Figure 12:
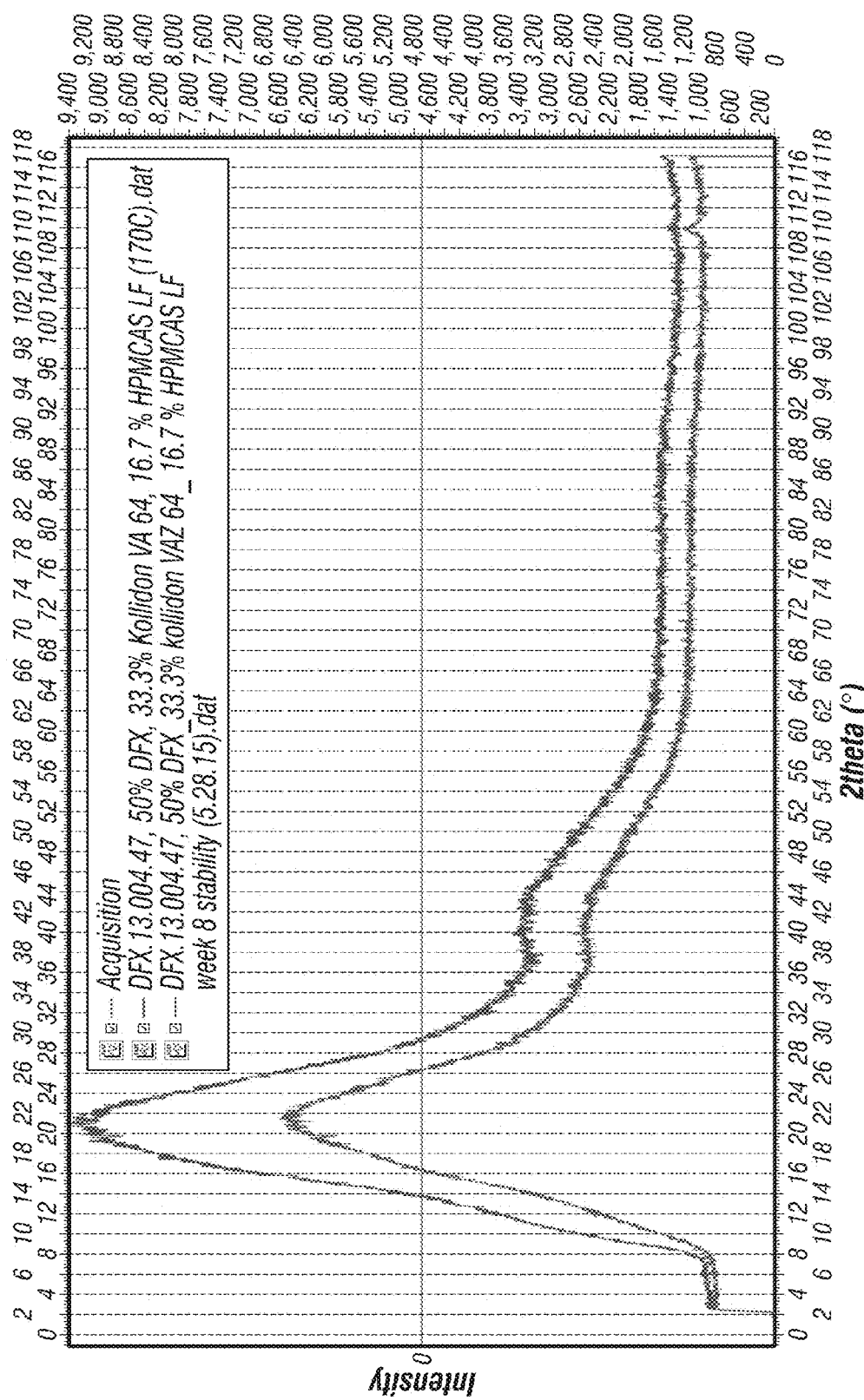
FIG. 12. XRD analysis of Lot 13-004-47 (50% DFX, 33.33% Copovidone, 16.67% HPMCAS-LF). The red line represents the initial state of the product and the green line represents the product following 8 weeks storage at 40° C., 75% RH (open containers). The absence of peaks corresponding to crystalline DFX demonstrates that the drug was substantially amorphous in the formulation at both conditions.

FIG. 2 shows a representative processing profile for an amorphous intermediate containing DFX and copovidone. The profile demonstrates that the time for which the drug and polymer were exposed to elevated temperatures was limited to about 3 seconds and the maximum processing temperature was 170° C.; approximately 95° C. below the melting point of DFX. As previously discussed, achieving an entirely amorphous DFX composition with high drug loading at the conditions of lot 79 is a surprising result unique to the KinetiSol® process. As stated above, limiting the duration and extent of thermal exposure is critical to achieving product of this composition with acceptable drug and polymer purity.

Example 2—Solid-State Analysis of KinetiSol® Processed Deferasirox Compositions by X-Ray Diffraction and Modulated Differential Scanning Calorimetry XRD Method and Results.

An Equinox 100 standalone bench top X-ray diffractometer (INEL, Inc., Stratham N.H.) was used to analyze the solid dispersions for presence of DFX crystallinity immediately after manufacture and on storage at accelerated conditions. Samples were placed in an aluminum crucible and loaded in a rotating sample holder. Samples were analyzed for 600 seconds using a Cu K radiation source ($\lambda$=1.5418 Å) operating at 42 kV and 0.81 mA.

Results provided in FIGS. 3-12 illustrate that substantially amorphous DFX solid dispersions of varying compositions were manufactured by KinetiSol®. Also contained in these figures are results demonstrating that these compositions remain amorphous on extended storage at accelerated conditions: 40° C./75% RH, open container. Consequently, this analysis confirmed that the KinetiSol® process is capable of generating amorphous solid dispersions of DFX at high drug loadings despite the high melting temperature of the compound that precludes the use of other thermal processing technologies.

mDSC method and results.

Modulated Differential Scanning calorimetry (mDSC) analyses were performed using a TA Instruments Model Q20 modulated differential scanning calorimeter (New Castle, Del.) operating under a high purity nitrogen flow rate of 50 ml/min. Sample aliquots were weighed into Tzero aluminum sample pans within a sample weight range of 10-15 mg. The pans were then capped with a Tzero lid and crimped using the Tzero sample press. The samples were analyzed by a modulated method in a temperature range from 25-310° C. at a ramp rate of 5° C./min, an amplitude of 1° C., and a period of 60 sec.

TABLE 2

Selected results of mDSC analysis for several amorphous DFX dispersions produced by KinetiSol ®

| Lot number | Composition | Glass transition temperature [° C.] |
|---|---|---|
| 13-004-37 | 40% API, 60% Copovidone | 120.7 |
| 13-004-38 | 40% API, 60% Copovidone | 119.5 |
| 13-004-40 | 60% API, 40% Copovidone | 115.9 |
| 13-004-50 | 40% API, 60% Eudragit L100-55 | 83.7 |
| 13-004-47 | 50% API, 33.3% Copovidone, 16.7% HPMCAS L | 110.6 |

The results presented in Table 2 illustrate that single-phase amorphous dispersions of DFX in various polymer systems were achieved by KinetiSol® as demonstrated by their single glass transition temperatures ($T_g$). Further, the $T_g$s for all systems are substantially greater than the anticipated maximum storage temperatures (~40° C.), suggesting that all systems will be physically stable for pharmaceutically relevant storage times (≤2 years). These $T_g$s are also substantially higher than what could be achieved for these systems when processing with other thermal technologies, if these technologies could be enabled by the introduction of plasticizers. With the addition of a plasticizer, the $T_g$s of the compositions would be substantially reduced, and correspondingly, the product shelf life.

Example 3—HPLC Analysis of KinetiSol® Processed Deferasirox Compositions

Deferasirox samples were analyzed for potency and impurities by reversed phase HPLC analysis. The standard and sample diluent was a 50/50 mixture of acetonitrile and methanol. Standards and samples were prepared at a concentration of 0.05 mg of deferasirox API per mL of solution. Brief sonication was performed, when necessary, to add with dissolving the samples. All samples were filtered through a 0.45 μm nylon syringe filter prior to analysis.

A 50 mM ammonium phosphate monobasic buffer with pH adjusted to 8.00 was used as mobile phase A and 100% acetonitrile was used as mobile phase B. The method utilized a gradient (below) to modulate mobile phase composition with a constant flow rate of 0.25 mL per minute. The total gradient run time was 14 minutes. Standard and assay sample injection volume was 2 μL and the impurities injection volume was 10 μL. Samples were maintained at ambient temperature. The column used was a Luna 2.5 um C18(2) HST column from Phenomenex, part number 00D-4446-B0, and was maintained at 40° C. during analysis. The detection wavelength for deferasirox was 247 nm with a typical deferasirox retention time of 3.3 minutes. Gradient method parameters are shown below:

| Time (minutes) | Mobile Phase A (%) | Mobile Phase B (%) |
|---|---|---|
| 0 | 70 | 30 |
| 2 | 70 | 30 |
| 9 | 20 | 80 |
| 10 | 20 | 80 |
| 11 | 70 | 30 |
| 14 | 70 | 30 |

The results of HPLC analysis shown in Table 3 reveal that all lots had purity values in excess of 99.5%, and most exceeded 99.9% purity. These data demonstrate that substantially amorphous dispersions of DFX in various polymer systems were able to be produced by KinetiSol® with negligible generation of process related impurities. This result is uniquely enabled by KinetiSol® owing to the short processing times and low temperatures at which a high drug load amorphous dispersion was achieved for the high-melting DFX.

TABLE 3

Summary of potency and purity analysis by HPLC for various KinetiSol® processed DFX amorphous solid dispersions

| Lot | Composition | Potency [% label claim] | Purity [% area] |
|---|---|---|---|
| 13-004-37 | 40% API, 60% Copovidone | 92.3 | 99.94 |
| 13-004-38 | 40% API, 60% Copovidone | 95.8 | 99.96 |
| 13-004-40 | 60% API, 40% Copovidone | 95.2 | 99.97 |
| 13-004-47 | 50% API, 33.33% Copovidone, 16.67% HPMCAS L | 94.8 | 99.95 |
| 13-004-50 | 40% API, 60% Eudragit L100-55 | 100.0 | 99.53 |
| 13-004-57 | 40% API, 30% Copovidone, 30% Eudragit L100-55 | 100.5 | 99.93 |

Example 4—Tableting or Encapsulation of KinetiSol® Processed Amorphous Intermediates of Deferasirox In order to assess the performance of various DFX amorphous solid dispersions relative to the commercial Exjade® and Jadenu® products, the amorphous intermediates was further processed into final dosage forms, i.e., tablets and capsules. The methods by which these tablets and capsules were produced and their quantitative compositions are provided below.

Tableting Procedure.

Milled DFX amorphous solid dispersions were blended in glass bottles with all non-lubricant excipients for 10 minutes in a MaxiBlend Lab Blender (GlobePharma, North Brunswick, N.J.) fitted with a bottle blending attachment. Lubricant was then added and the mixture blended for an additional 5 minutes. Individual portions of the blend were weighed and compressed into 9.28 mm×19 mm modified capsule shaped tablets, (unless stated otherwise) at 3,000-4,000 psig compression force using a Manual Tablet Compaction Machine (MTCM-1, Globe Pharma, Inc., New Brunswick, N.J.).

TABLE 4

Tablet composition of Lot 13.004.73 - for dissolution analysis.

| Component | % w/w | mg/tablet |
|---|---|---|
| Lot 13-004-58 | 90.0 | 720.0 |
| Microcrystalline cellulose | 5.0 | 40.0 |
| Croscarmellose | 3.0 | 24.0 |
| Sodium chloride | 1.5 | 12.0 |
| Magnesium stearate | 0.5 | 4.0 |
| Total | 100.0 | 800.0 |

TABLE 5

Tablet composition of Lot 13.004.74 - for dissolution analysis

| Component | % w/w | mg/tablet |
|---|---|---|
| Lot 13-004-58 | 99.5 | 716.4 |
| Magnesium stearate | 0.5 | 3.6 |
| Total | 100.0 | 720.0 |

TABLE 6

Tablet composition of Lot 13.004.75 - for dissolution analysis

| Component | % w/w | mg/tablet |
|---|---|---|
| Lot 13-004-60 | 90.0 | 720.0 |
| Microcrystalline cellulose | 5.0 | 40.0 |
| Croscarmellose | 3.0 | 24.0 |
| Sodium chloride | 1.5 | 12.0 |
| Magnesium stearate | 0.5 | 4.0 |
| Total | 100.0 | 800.0 |

TABLE 7

Tablet composition of Lot 13.004.76 - for dissolution analysis

| Component | % w/w | mg/tablet |
|---|---|---|
| Lot 13-004-60 | 99.5 | 716.4 |
| Magnesium stearate | 0.5 | 3.6 |
| Total | 100.0 | 720.0 |

TABLE 8

Tablet composition of Lot 13.004.77 - for dissolution analysis

| Component | % w/w | mg/tablet |
|---|---|---|
| Lot 13-004-50 | 90.0 | 900.0 |
| Microcrystalline cellulose | 5.0 | 50.0 |
| Croscarmellose | 3.0 | 30.0 |
| Sodium chloride | 1.5 | 15.0 |
| Magnesium stearate | 0.5 | 5.0 |
| Total | 100.0 | 1000.0 |

TABLE 9

Tablet composition of Lot 13.004.78 - for dissolution analysis

| Component | % w/w | mg/tablet |
|---|---|---|
| Lot 13-004-50 | 99.5 | 895.5 |
| Magnesium stearate | 0.5 | 4.5 |
| Total | 100.0 | 900.0 |

TABLE 10

Lots 13.004.84.1-4: Tablets of different geometries for dissolution testing

| Component | #1 | #2 | #3 | #4 |
|---|---|---|---|---|
| Lot 13-004-40 [mg] | 600.0 | 600.0 | 600.0 | 200 |
| Mannitol [mg] | — | — | 66.7 | — |
| Tablet tooling | Modified capsule 9.28 mm × 19 mm | Round flat 15 mm diameter | Modified capsule 9.28 mm × 19 mm | Round concave 7.5 mm diameter |

Encapsulation Procedure.

Capsules containing DFX milled amorphous intermediate were prepared by manually filling a pre-weighed aliquot of the amorphous intermediate, equivalent to 180 mg of DFX, into size 0 hard gelatin capsules. Two capsules, equivalent to 360 mg of DFX, were used for in vitro dissolution testing.

Example 5—In Vitro Dissolution Analysis of Tablet and Capsules Containing KinetiSol® Processed Amorphous Intermediates of Deferasirox The dissolution properties of various Deferasirox samples were investigated using a USP Apparatus 2 dissolution tester with reversed phase HPLC method for quantification. 0.1N HCl (pH 1.1) and 0.2M sodium phosphate tribasic solutions were prepared for dissolution media. Both were degassed and preheated prior to use. Additionally, a diluent composed of 50/50 acetonitrile/water was prepared for dissolution sample dilution. A standard was prepared at a nominal concentration of 0.05 mg deferasirox API per mL of solution using an appropriate combination of dissolution media and diluent to dissolve. 750 mL of 0.1N HCl was added to each vessel of analysis and allowed to equilibrate to 37° C. An equivalent of 360 mg of deferasirox API was added to each vessel and paddle revolution was initiated at 50 rpm. At 1 and 2 hours, 5 mL aliquots were pulled from each vessel of analysis and filtered through 0.45 µm nylon syringe filters. Immediately after the 2 hour pull, 250 mL of pre-heated 0.2M sodium phosphate tribasic solution was rapidly added to each vessel of analysis to yield a pH of 6.8. At 2.25, 2.5, 3, 4, 6, and 8 hour total run time, 5 mL aliquots were pulled from each vessel of analysis and filtered through 0.45 µm nylon syringe filters. All filtered samples were rapidly diluted with diluent using a dilution factor of 10 and then transferred to HPLC vials for analysis.

A 50 mM ammonium phosphate monobasic buffer with pH adjusted to 8.00 was used as mobile phase A and 100% acetonitrile was used as mobile phase B. The method utilized an isocratic ratio of 60/40 mobile phase A/mobile phase B with a constant flow rate of 0.25 mL per minute. The total gradient run time was 4 minutes. Standard and sample injection volume was 2 µL and the samples were maintained at ambient temperature. The column used was a Luna 2.5 um C18(2) HST column from Phenomenex, part number 00D-4446-B0, and was maintained at 40° C. during analysis. The detection wavelength for deferasirox was 247 nm with a typical deferasirox retention time of 2.0 minutes.

Figure 13:
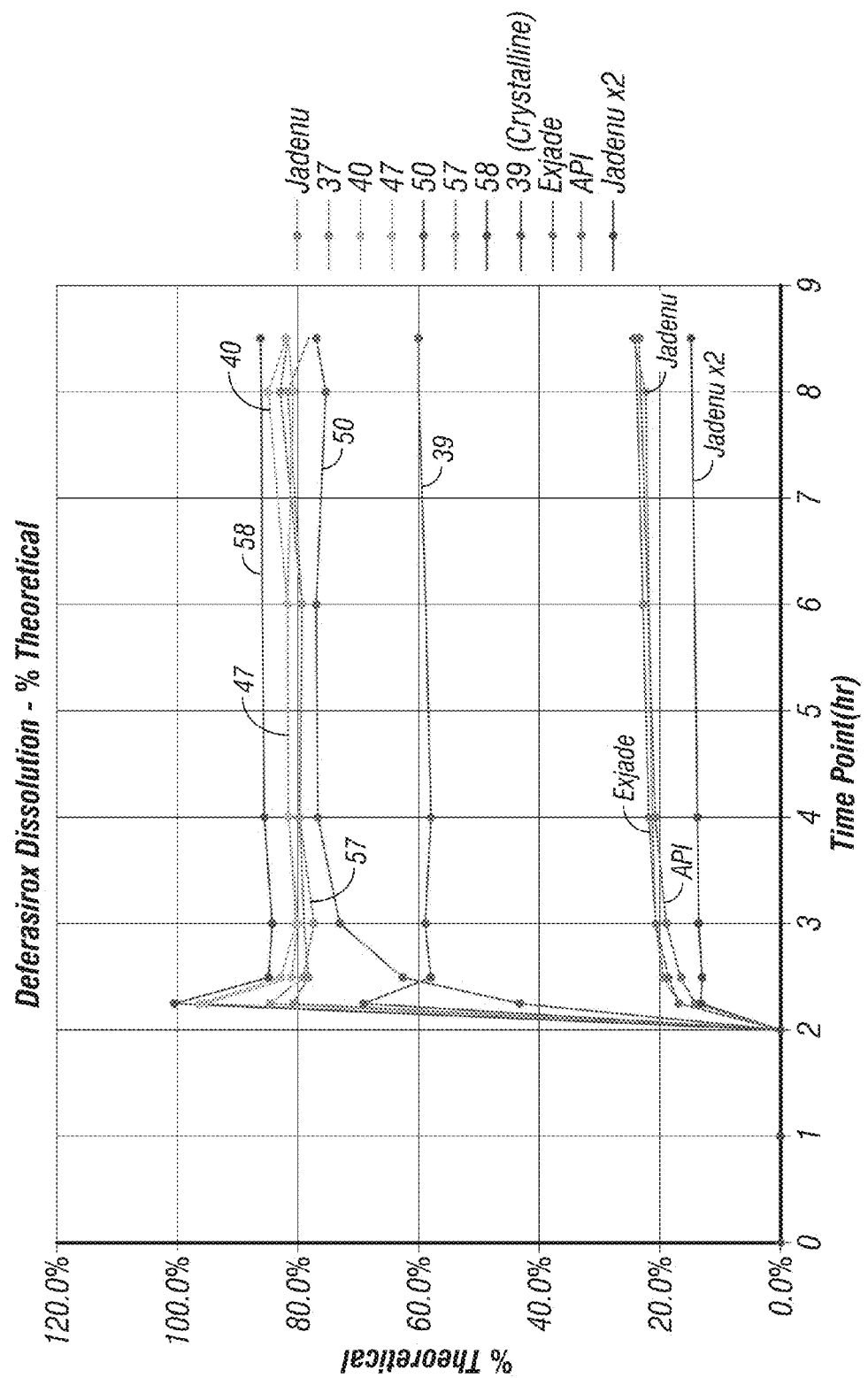
FIG. 13. Dissolution profiles of comparators (Jadenu® and Exjade®), pure API and amorphous intermediates in capsules. Jadenu®—360 mg tablet of Jadenu®; Jadenu® x2—Two 360 mg capsules of Jadenu®, 720 mg total; API—Two capsules of 180 mg neat API, 360 mg total; 37—Two capsules containing lot 13-004-37 (40% API, 60% Copovidone) amorphous intermediate, equivalent to 360 mg DFX total; 40—Two capsules containing lot 13-004-40

FIG. 13 shows dissolution results comparing pure DFX API, Jadenu®, Exjade® and several amorphous DFX solid dispersions filled into capsules. All formulations tested exhibit minimal release during the first 2 hours of the test (the acid phase) due to the highly insoluble nature of DFX in acidic media. Following the media change to pH 6.8 buffer, all of the crystalline DFX articles (pure API, Jadenu®, and Exjade®) show relative fast, yet limited release, with no composition releasing more than about 25% of its theoretical drug content. This result is surprising because based on the reported water solubility for DFX, 400 mg of the drug should be soluble in the neutral phase of this dissolution test; therefore, it is unclear why the crystalline formulations would begin to reach an asymptote for drug release near 20%. All KinetiSol® processed formulations exhibited rapid and extensive dissolution relative to the crystalline controls, including lot 39 which was partially crystalline. All substantially amorphous formulations converged to a limit of about 80% release of the theoretical drug content; approximately four-fold greater than the crystalline DFX control samples. With the exception of lot 50, all substantially amorphous DFX formulations reached their maximum drug concentrations by the first time point, illustrating extremely rapid dissolution with formulations containing copovidone. Lot 50, containing only Eudragit L100-55 and DFX, exhibited a somewhat slower release rate relative to the other amorphous compositions, but reached near the same plateau concentration.

The dissolution results provided in FIG. 14 demonstrate the different release profiles that can be achieved by formulating the various DFX amorphous intermediates as disintegrating or eroding tablets. The rapidly disintegrating tablets show very similar DFX release to the amorphous intermediates, while eroding tablets can be produced with substantially reduced release rates. If this release modulation in vitro translates to tunable pharmacokinetic profiles in vivo, it would represent a significant advantage for the compositions of the current disclosure as it could potentially enable achievement of the most therapeutically beneficial PK profile.

The results shown in FIG. 15 demonstrate the effect of tablet geometry on the release rate of an eroding tablet containing a DFX:Copovidone (60:40 w/w) amorphous dispersion. These results suggest that altering tablet surface area provides another mode by which the release rate of an eroding amorphous DFX tablet can be adjusted.

Example 6—Pharmacokinetic Evaluation in Dogs of Tablet and Capsules Containing KinetiSol® Processed Amorphous Intermediates of Deferasirox Pharmacokinetic analysis following oral administration of three prototype DFX formulations containing novel DFX amorphous dispersion compositions and Jadenu (control) was conducted in male beagle dogs. Each group of dogs (n=4) was fasted overnight prior to dosing; food was returned after the 4 hour post dose blood collection. Each animal, weight 8 to 12 kg, was dosed with a single unit containing 360 mg DFX. Sodium heparin was used as an anti-coagulant for 1 mL blood samples that were collected by direct venipuncture of a cephalic vein and placed at 2-8° C. on wet ice. Samples were collected at 0.5, 1, 1.5, 2, 3, 4, 6, 12, 24, and 48 hr, post dose. Samples were centrifuged at 3500 rpm to isolate plasma for 10 minutes at 2 to 8° C. The resulting plasma was transferred to individual polypropylene tubes and immediately placed on dry ice until storage at nominally −20° C. for analysis. The plasma samples were analyzed for total DFX species (free and iron-bound DFX) concentration using a Research Grade LC-MS/MS Assay. Linear Trapezoidal non-compartmental pharmacokinetic analysis was performed in WinNonlin Version 2.1. The quantitative compositions of the formulations testing and the results of the canine pharmacokinetic analysis are provided in Tables 11-13.

TABLE 11

Quantitative composition of Formulation 1 (eroding tablet)

| Component | % w/w | mg/tablet |
|---|---|---|
| Lot 13-004-79 | 99.50 | 720.00 |
| Magnesium stearate | 0.50 | 3.62 |
| Total | 100.00 | 723.62 |

TABLE 12

Quantitative composition of Formulation 2 (disintegrating tablet)

| Component | % w/w | mg/tablet |
|---|---|---|
| Lot 13-004-79 | 80.0 | 720.00 |
| Microcrystalline cellulose | 12.0 | 108.00 |
| Croscarmellose | 5.0 | 45.00 |
| Sodium chloride | 2.5 | 22.50 |
| Magnesium stearate | 0.5 | 4.50 |
| Total | 100.0 | 900.00 |

TABLE 12

Quantitative composition of Formulation 3 (capsule)

| Component | % w/w | mg/capsule |
|---|---|---|
| Lot 13-004-50 | 100.0 | 900.0 |

TABLE 13

Pharmacokinetic parameters following oral administration of new DFX amorphous dispersion formulations and the commercial product, Jadenu ® (control)

| | | Jadenu (Group 1) | | Formulation 1 (Group 2) | | Formulation 2 (Group 3) | | Formulation 3 (Group 4) | |
|---|---|---|---|---|---|---|---|---|---|
| | | Mean (ng/mL) | SD (ng/mL) | Mean (ng/mL) | SD (ng/mL) | Mean (ng/mL) | SD (ng/mL) | Mean (ng/mL) | SD (ng/mL) |
| $AUC_{(0-x)}$ | hr · ng/mL | 117,075.00 | 29,729.15 | 54,475.00 | 10,155.91 | 184,975.00 | 92,725.06 | 168,500.00 | 26,888.66 |
| $AUC_{(0-\infty)}$ | hr · ng/mL | 117,750.00 | 29,590.26 | 54,825.00 | 10,247.72 | 186,075.00 | 93,295.35 | 169,250.00 | 26,874.71 |
| % AUC Extrap | % | 0.627 | 0.425 | 0.627 | 0.318 | 0.592 | 0.133 | 0.454 | 0.315 |
| Cmax | ng/mL | 24,100.00 | 5,405.55 | 7,897.50 | 1,214.86 | 53,825.00 | 24,062.33 | 32,925.00 | 10,679.07 |
| tmax | hr | 1.75 | 0.289 | 1.88 | 0.250 | 1.00 | 0.408 | 1.13 | 0.250 |
| Terminal $t_{1/2}$ | hr | 8.55 | 0.992 | 7.49 | 1.42 | 8.93 | 0.793 | 7.63 | 1.16 |
| Rel. BA | % | 100% | NA | 47% | NA | 158% | NA | 144% | NA |

These results show that Formulations 2 and 3 improved the bioavailability of DFX relative to Jadenu® by 58% and 44% (based on mean $AUC_{0-\infty}$), respectively. Formulation 3 was also found to provide reduced variability of total DFX exposure ($AUC_{0-\infty}$) relative to Jadenu®. Formulation 1, which was designed for extended DFX release from an eroding tablet, was found to provide substantially lower oral absorption relative to Jadenu® (47% of mean $AUC_{0-\infty}$).

The PK results in conjunction with the in vitro dissolution results demonstrate the substantial advantages of the amorphous dispersion formulations of DFX with regard to enhancing dissolution properties and oral bioavailability. Considering that Formulations 1 and 2 contain the identical amorphous solid dispersion formulation (50% DFX, 50% copovidone) and it is only the tablet design that differs, it is evident that the PK performance with this intermediate can be modulated by simply adjusting the external-phase of the tablet composition and geometry of the eroding tablet. This feature provides the capability of tuning the final dosage form to achieve a wide range of potentially desirable PK profiles.

Example 7—Pharmacokinetic Experiments in Humans

In vivo human studies were performed to evaluate and compare the oral bioavailability and the maximum deferasirox plasma concentrations achieved after administration of two Test deferasirox formulations with results obtained with Jadenu™ tablets (deferasirox), when administered as a single oral dose in healthy subjects under fasting conditions. Also, the effect of food on Test deferasirox 360 mg tablet formulations no. 30011 and no. 30012, a comparison of $T_{max}$, $t_{1/2}$ and other pharmacokinetic parameters among the different deferasirox dosage forms in healthy subjects under fasting and fed conditions, and monitoring of the safety of single doses of each Test deferasirox formulation and Jadenu™, when administered to healthy subjects under fasting and/or fed conditions, was conducted.

The study was a single center, randomized, single dose, laboratory-blinded, 3-period, 3-sequence, crossover format. Twenty-four patients were planned for inclusion (12 subjects in each arm) and the study was fully enrolled. On patient discontinued, and 24 patients were analyzed. Twenty-four patients were considered in the pharmacokinetic and statistical analysis (subject 013, Period 3 was excluded from the food effect of treatment-6 and treatment-5 comparison), and 24 patients were considered in the safety analysis.

Subjects were male or female, at least 18 years of age but not older than 60 years. The main inclusion criteria were:
- light, non- or ex-smokers
- body mass index (BMI) ≥20.00 kg/m² and <30.00 kg/m²
- body weight of at least 65 kg but below 90 kg
- no clinically significant abnormality found in the 12-lead ECG performed at study entry
- negative pregnancy test for female subjects
- healthy according to medical history, complete physical examination (including vital signs) and laboratory tests (general biochemistry, hematology and urinalysis)

Test 1 used deferasirox (Formulation no. 30011) produced according to the methods described in Example 1. A tablet dosage form for oral administration was administered in a single dose of 14 mg/kg, rounded to the nearest whole 360 mg tablet. The batch no. was 15L001.

Test 2 used deferasirox (Formulation no. 30012) produced according to the methods described in Example 1. A tablet dosage form for oral administration was administered in a single dose of 14 mg/kg, rounded to the nearest whole 360 mg tablet. The batch no. was 15L002.

Reference product was Jadenu™ (deferasirox). A tablet dosage form for oral administration was administered in a single dose of 14 mg/kg, rounded to the nearest whole 360 mg tablet. The batch no. was F0007.

Treatments for Arm 1 (subjects 001 to 012) were as follows:

Treatment-1: The Test-1 formulation orally administered with 240 mL of water in the morning after a 10-hour overnight fast Treatment-2: The Reference formulation orally administered with 240 mL of water in the morning after a 10-hour overnight fast Treatment-3: The Test-1 formulation orally administered with 240 mL of water in the morning after a 10-hour overnight fast, thirty minutes after the start of a high-fat, high-calorie breakfast.

Treatments for Arm 2 (subjects 013 to 024) were as follows:

Treatment-4: The Test-2 formulation orally administered with 240 mL of water in the morning after a 10-hour overnight fast Treatment-5: The Reference formulation orally administered with 240 mL of water in the morning after a 10-hour overnight fast Treatment-6: The Test-2 formulation orally administered with 240 mL of water in the morning after a 10-hour overnight fast, thirty minutes after the start of a high-fat, high-calorie breakfast.

A single 14 mg/kg of deferasirox, rounded to the nearest whole 360 mg tablet, was administered under fasting (Treatment-1, Treatment-2, Treatment-4, and Treatment-5) and fed (Treatment-3 and Treatment-6) conditions in each study period. The drug administrations were separated by a wash-out of 7 calendar days.

In each study period, 19 blood samples were collected. The first blood sample was collected prior to drug administration while the others were collected up to 48 hours after the drug administration.

Analysis for deferasirox in human plasma was performed using HPLC with MS/MS detection. The assay range was 0.100 µg/mL to 100.000 µg/mL.

Safety was evaluated through assessment of adverse events, standard laboratory evaluations, vital signs, and physical examination.

The main absorption and disposition parameters were calculated using a non-compartmental approach with a log-linear terminal phase assumption. The trapezoidal rule was used to estimate area under the curve. The terminal phase estimation was based on maximizing the coefficient of determination. The pharmacokinetic parameters of this trial were $C_{max}$, $T_{max}$, $AUC_{0-T}$, $AUC_{0-\infty}$, $AUC_{0-T/\infty}$, $\lambda_Z$, $CL_{TOT}/F$, $V_D/F$ and $T_{half}$.

The statistical analysis was based on a parametric ANOVA model of the pharmacokinetic parameters; the two-sided 90% confidence interval of the ratio of geometric means for the $C_{max}$, $AUC_{0-T}$ and $AUC_{0-\infty}$ was based on ln-transformed data; the $T_{max}$ was rank-transformed.

ANOVA model was applied and used the fixed factors of sequence, period, treatment, and a random factor of the subject (nested within sequence).

The food effect was determined by comparing the $C_{max}$, $AUC_{0-T}$, $AUC_{0-\infty}$ and $T_{max}$ obtained for the fasted and fed conditions after administration of the Test-1 and Test-2 products. Deferasirox administered under fasted conditions will be considered the reference treatment and deferasirox administered with a high-fat meal will be considered the test treatment. An absence of food effect on the pharmacokinetic profile of the Test product is indicated when:

For the Test-1, the ratio of geometric LSmeans with corresponding 90% confidence interval calculated from the exponential of the difference between the Treatment-3 and Treatment-1 for the ln-transformed parameters $C_{max}$, $AUC_{0-T}$ and $AUC_{0-\infty}$ were all to be within the 80.00 to 125.00% bioequivalence range.

For the Test-2, The ratio of geometric LSmeans with corresponding 90% confidence interval calculated from the exponential of the difference between the Treatment-6 and Treatment-4 for the ln-transformed parameters $C_{max}$, $AUC_{0-T}$ and $AUC_{0-\infty}$ were all to be within the 80.00 to 125.00% bioequivalence range.

The results of these studies are shown in the following tables.

TABLE 14

Pharmacokinetic parameters for Treatment 1 (Formulation 30011, fasted) versus Treatment 2 (Jadenu reference, fasted)

| PARAMETER | Treatment-1 (Test-1-#30011, Fast) (n = 12) | | Treatment-2 (Reference Jadenu ™) (n = 12)[b] | |
|---|---|---|---|---|
| | MEAN | C.V. (%) | MEAN | C.V. (%) |
| $C_{max}$ (µg/mL) | 55.636 | (25.4) | 45.071 | (38.8) |
| ln ($C_{max}$) | 3.9878 | (6.6) | 3.7284 | (11.7) |
| $T_{max}$ (hours)[a] | 3.50 | (2.50-5.00) | 2.50 | (1.50-5.00) |
| $AUC_{0-T}$ (µg · h/mL) | 553.883 | (28.8) | 489.876 | (42.9) |
| ln ($AUC_{0-T}$) | 6.2794 | (4.6) | 6.1223 | (6.3) |
| $AUC_{0-\infty}$ (µg · h/mL) | 590.016 | (31.9) | 542.527 | (46.4) |
| ln ($AUC_{0-\infty}$) | 6.3353 | (4.9) | 6.2127 | (6.7) |
| $AUC_{0-T/\infty}$ (%) | 94.66 | (4.6) | 92.86 | (5.2) |
| $\lambda_Z$ (hours⁻¹) | 0.0668 | (38.9) | 0.0612 | (39.9) |
| $T_{half}$ (hours) | 11.63 | (34.6) | 12.80 | (33.2) |
| $V_D/F$ (L) | 31.82 | (33.7) | 41.63 | (49.0) |
| $Cl_{TOT}/F$ (L/h) | 2.00 | (29.8) | 2.32 | (36.8) |

[a]Median (range)
[b]n = 11 for $\lambda_Z$, $AUC_{0-\infty}$, $AUC_{0-T/\infty}$, $T_{half}$, $V_D/F$ and $Cl_{TOT}/F$

TABLE 15

Pharmacokinetic parameters for Treatment 3 (Formulation 30011, fed) versus Treatment 1 (Formulation 30011, fasted)

| PARAMETER | INTRA-SUBJECT C.V. (%) | GEOMETRIC LSMEANS * | | RATIO (%) | 90% CONFIDENCE LIMITS (%) | |
|---|---|---|---|---|---|---|
| | | Treatment-3 (30011, Fed) (n = 12) | Treatment-1 (30011, Fast) (n = 12) | | LOWER | UPPER |
| $C_{max}$ | 28.3 | 43.56 | 53.937 | 80.75 | 66.43 | 98.16 |
| $AUC_{0-T}$ | 16.0 | 518.77 | 533.468 | 97.24 | 86.95 | 108.76 |
| $AUC_{0-\infty}$ | 14.5 | 553.25 | 564.131 | 98.07 | 88.60 | 108.55 |

<sup>a</sup>units are µg/mL for $C_{max}$ and µg · h/mL for $AUC_{0-T}$ and $AUC_{0-\infty}$

TABLE 16

Pharmacokinetic parameters for Treatment 4 (Formulation 30012, fasted) versus Treatment 5 (Jadenu reference, fasted)

| PARAMETER | Treatment-4 (30012, Fast) (n = 12)$^b$ | | Treatment-5 (Reference Jadenu ™) (n = 12)$^b$ | |
|---|---|---|---|---|
| | MEAN | C.V. (%) | MEAN | C.V. (%) |
| $C_{max}$ (µg/mL) | 58.019 | (27.2) | 45.538 | (26.8) |
| ln ($C_{max}$) | 4.0228 | (7.4) | 3.7862 | (7.0) |
| $T_{max}$ (hours)$^a$ | 4.00 | (2.50-5.00) | 3.00 | (2.00-4.00) |
| $AUC_{0-T}$ (µg · h/mL) | 539.847 | (30.4) | 472.468 | (34.6) |
| ln ($AUC_{0-T}$) | 6.2473 | (5.0) | 6.0971 | (6.2) |
| $AUC_{0-\infty}$ (µg · h/mL) | 556.538 | (31.8) | 499.076 | (33.8) |
| ln ($AUC_{0-\infty}$) | 6.2755 | (5.1) | 6.1547 | (6.0) |
| $AUC_{0-T/\infty}$ (%) | 95.40 | (2.7) | 95.48 | (6.3) |
| $\lambda_Z$ (hours$^{-1}$) | 0.0694 | (30.0) | 0.0748 | (27.5) |
| $T_{half}$ (hours) | 10.70 | (25.1) | 10.26 | (42.1) |
| $V_D/F$ (L) | 33.02 | (46.6) | 37.17 | (67.2) |
| $Cl_{TOT}/F$ (L/h) | 2.13 | (32.2) | 2.45 | (39.1) |

<sup>a</sup>Median (range)
<sup>b</sup>n = 11 for $\lambda_Z$, $AUC_{0-\infty}$, $AUC_{0-T/\infty}$, $T_{half}$, $V_D/F$ and $Cl_{TOT}/F$

TABLE 17

Pharmacokinetic parameters for Treatment 6 (Formulation 30012, fed) versus Treatment 4 (Formulation 30012, fasted)

| PARAMETER | INTRA-SUBJECT C.V. (%) | GEOMETRIC LSMEANS* | | RATIO (%) | 90% CONFIDENCE LIMITS (%) | |
|---|---|---|---|---|---|---|
| | | Treatment-6 (30012, Fed) (n = 11)$^b$ | Treatment-4 (30012, Fast) (n = 12)$^c$ | | LOWER | UPPER |
| $C_{max}$ | 18.9 | 55.86 | 39.45 | 70.63 | 61.59 | 81.00 |
| $AUC_{0-T}$ | 14.3 | 516.62 | 449.18 | 86.95 | 78.35 | 96.49 |
| $AUC_{0-\infty}$ | 14.7 | 532.52 | 468.27 | 87.93 | 78.61 | 98.37 |

<sup>a</sup>units are µg/mL for Cmax and µg · h/mL for $AUC_{0-T}$ and $AUC_{0-\infty}$
<sup>b</sup>n = 10 $AUC_{0-\infty}$ for Treatment-6
<sup>c</sup>n = 11 $AUC_{0-\infty}$ for Treatment-4

The PK parameters provided in Table 14 demonstrate that Formulation 30011 (a composition made according to methods described in Example 1) showed superior pharmacokinetic performance in fasted human subjects relative to the reference formulation, Jadenu®. Specifically, the $C_{max}$ value was determined to be 30% greater and the total oral absorption, as indicated by $AUC_{0-T}$ and $AUC_{inf}$, was 17% and 13% greater than Jadenu®, respectively. The superior PK profile of formulation 30011 versus Jadenu® can also be observed qualitatively from FIG. 16. From this figure, the enhanced $C_{max}$ and AUC can be readily recognized by comparing the plasma concentration versus time plots for Treatment 1 (30011) to Treatment 2 (Jadenu®). A reduction in pharmacokinetic variability was also observed for the 30011 formulation relative to Jadenu® as indicated by the percent C.V. values for $C_{max}$ and $AUC_{0-\infty}$. For $C_{max}$, the percent C.V. values were 25.4% and 38.8% for 30011 and Jadenu®, respectively; and for $AUC_{0-\infty}$ the percent C.V. values were 31.9% and 46.4% for 30011 and Jadenu® respectively. Upon examination of FIG. 17, it can be seen that formulation 30011 performed similarly or better than Jadenu® for all subjects in the study, with the exception of Subject 3. For subjects 5, 7, 9, and 12; the total oral absorption with 30011 was found to be substantially better that Jadenu®. This provides some evidence that the compositions of this invention could provide a significant improvement in the therapeutic efficacy of DFX in patients who have been observed to be poor absorbers of crystalline DFX. Finally, the results shown in Table 15 demonstrate that formulation 30011 has a negligible food effect when comparing the fasted results to those when the formulation is administered following a high fat meal. Specifically, the ratio of AUCs between the fed and fasted state are greater than 97%. In summary, formulation 30011 was demonstrated by these experiments in healthy human subjects to have superior PK performance relative to Jadenu in the fasted state and to have essentially no food effect on drug absorption.

The PK parameters provided in Table 16 demonstrate that Formulation 30012 (a composition made according to methods described in Example 1) showed superior pharmacokinetic performance in fasted human subjects relative to the reference formulation, Jadenu®. Specifically, the $C_{max}$ value was determined to be 27% greater and the total oral absorption, as indicated by $AUC_{0-T}$ and $AUC_{inf}$, was 16% and 13% greater than Jadenu®, respectively. The superior PK profile of formulation 30012 versus Jadenu® can also be observed qualitatively from FIG. 16 From this Figure, the enhanced $C_{max}$ and AUC can be readily recognized by comparing the plasma concentration versus time plots for Treatment 4 (30012) to Treatment 5 (Jadenu®). Finally, the results shown in Table 17 demonstrate that formulation 30012 has a limited food effect when comparing the fasted results to those when the formulation is administered following a high fat meal. Specifically, the ratio of AUCs between the fed and fasted state are greater than 87%. In summary, formulation 30012 was demonstrated by these experiments in healthy human subjects to have superior PK performance relative to Jadenu® in the fasted state and to have limited food effect on drug absorption.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

V. References

The following references, to the extent that they provide exemplary procedural or other details supplementary to those set forth herein, are specifically incorporated herein by reference.

1. NICK H et al. ICL670A: Preclinical Profile. In: Hershko, C. ed. *Iron Chelation Therapy*. Springer US, 2002: 185-203.
2. FAN C et al. Impact of polymers on dissolution performance of an amorphous gelleable drug from surface-coated beads. *European Journal of Pharmaceutical Sciences* 2009; 1: 1-10.
3. CHIRNOMAS D et al. *Deferasirox pharmacokinetics in patients with adequate versus inadequate response*, 114, 2009.
4. WALDMEIER F et al. Pharmacokinetics, Metabolism, and Disposition of Deferasirox in β-Thalassemic Patients with Transfusion-Dependent Iron Overload Who Are at Pharmacokinetic Steady State. *Drug Metabolism and Disposition* 2010; 5: 808-816.
5. DINUNZIO J C et al. Production of advanced solid dispersions for enhanced bioavailability of itraconazole using KinetiSol® Dispersing. *Drug Development and Industrial Pharmacy* 2010; 9: 1064-1078.
6. MILLER D et al. Targeted Intestinal Delivery of Supersaturated Itraconazole for Improved Oral Absorption. *Pharm Res* 2008; 6: 1450-1459.
7. MILLER D A et al. Enhanced In Vivo Absorption of Itraconazole via Stabilization of Supersaturation Following Acidic-to-Neutral pH Transition. *Drug Dev Ind Pharm* 2008; 8: 890-902.
8. HUGHEY J R et al. Thermal processing of a poorly water-soluble drug substance exhibiting a high melting point: The utility of KinetiSol® Dispersing. *International Journal of Pharmaceutics* 2011; 1-2: 222-230.
9. HUGHEY J et al. Dissolution Enhancement of a Drug Exhibiting Thermal and Acidic Decomposition Characteristics by Fusion Processing: A Comparative Study of Hot Melt Extrusion and KinetiSol® Dispersing. *AAPS PharmSciTech* 2010; 2: 760-774.
10. BENNETT R C et al. Preparation of amorphous solid dispersions by rotary evaporation and KinetiSol Dispersing: approaches to enhance solubility of a poorly water-soluble gum extract. *Drug Development and Industrial Pharmacy* 2013; 0: 1-16.

What is claimed:

1. A pharmaceutical composition comprising an amorphous solid dispersion of deferasirox (DFX) and one or more pharmaceutically acceptable excipients, wherein said composition has a single glass transition temperature.

2. The pharmaceutical composition of claim 1, wherein said composition remains amorphous per x-ray diffraction analysis following storage in an open container at about 40° C., relative humidity of about 75%, at five weeks.

3. The pharmaceutical composition of claim 1, wherein the one or more pharmaceutically acceptable excipients comprises one or more polymers, a processing agent and/or a surfactant.

4. The pharmaceutical composition of claim 3, wherein the one or more pharmaceutical polymers comprises an agent selected from the group consisting of poly(vinyl acetate)-co-polyvinylpyrrolidone) copolymer, ethylcellulose, hydroxypropylcellulose, cellulose acetate butyrate, poly(vinylpyrrolidone), poly(ethylene glycol), poly(ethylene oxide), poly(vinyl alcohol), hydroxypropyl methylcellulose, ethylcellulose, hydroxyethylcellulose, sodium carboxymethyl-cellulose, dimethylaminoethyl methacrylate-methacrylic acid ester copolymer, ethylacrylate-methylmethacrylate copolymer, cellulose acetate phthalate, cellulose acetate trimelletate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropylmethylcellulose acetate succinate and polyvinyl caprolactam-polyvinyl acetate-polyethylene glycol graft copolymer.

5. The pharmaceutical composition of claim 3, wherein the surfactant comprises an agent selected from the group consisting of sodium dodecyl sulfate, dioctyl sodium sulphosuccinate, polyoxyethylene (20) sorbitan monooleate, glycerol polyethylene glycol oxystearate-fatty acid glycerol polyglycol esters-polyethylene glycols-glycerol ethoxylate, glycerol-polyethylene glycol ricinoleate-fatty acid esters of polyethyleneglycol-polyethylene glycols-ethoxylated glycerol, vitamin E TPGS, and sorbitan laurate, and the pharmaceutical polymer comprises an agent selected from a group consisting of poly(vinylpyrrolidone), hydroxypropylcellulose, poly(vinyl alcohol), hydroxypropyl methylcellulose, hydroxyethylcellulose, and sodium carboxymethylcellulose and polyvinyl caprolactam-polyvinyl acetate-polyethylene glycol graft copolymer.

6. The pharmaceutical composition of claim 3, wherein the one or more pharmaceutical polymers is/are a water soluble polymer(s).

7. The pharmaceutical composition of claim 6, wherein the one or more pharmaceutical water soluble polymer(s) is/are selected from the group consisting of poly(vinyl acetate)-co-poly(vinylpyrrolidone) copolymer, poly(vinylpyrrolidone), cellulose acetate phthalate, poly(vinyl acetate) phthalate, hydroxypropylmethylcellulose phthalate, poly(methacrylate ethylacrylate) (1:1) copolymer, poly (methacrylate methylmethacrylate) (1:1) copolymer, poly (methacrylate methylmethacrylate) (1:2) copolymer, hydroxypropyl methylcellulose, hydroxypropylmethylcellulose acetate succinate, poly(vinyl alcohol), and polyvinyl caprolactam-polyvinyl acetate-polyethylene glycol graft copolymer.

8. The pharmaceutical composition of claim 6, wherein the DFX to water soluble pharmaceutical polymer ratio is about 2:3, 1:1, or 3:2.

9. The pharmaceutical composition of claim 1, wherein the composition exhibits a drug loading of about 30%-60% DFX, about 40%-60% DFX, about 30% DFX, 35% DFX, 40% DFX, 45% DFX, 50% DFX, 55% DFX, or 60% DFX.

10. The pharmaceutical composition of claim 1, wherein the composition has less than about 1.0% degradation products of deferasirox (DFX).

11. The pharmaceutical composition of claim 1, wherein the purity of DFX used in said composition is about 95%, is about 99%, is about 99.5%, or is about 95% to about 100%.

12. The pharmaceutical composition of claim 1, wherein said pharmaceutical composition does not contain a processing agent, and/or does not contain a plasticizer.

13. The pharmaceutical composition of claim 1, wherein said pharmaceutical composition comprises about 90 mg DFX, about 125 mg DFX, about 250 mg DFX, about 360 mg DFX, or about 500 mg DFX.

14. The pharmaceutical composition of claim 1, wherein the one or more pharmaceutically acceptable excipients comprises a pharmaceutical polymer of high melt viscosity or a thermally labile pharmaceutical polymer.

15. The pharmaceutical composition of claim 1, wherein the purity of said composition is about 95%, is about 99%, is about 99.5%, or is about 95% to about 100%.

16. The pharmaceutical composition of claim 1, wherein the peak solubility of the DFX in the composition is greater than 400 µg/mL in an aqueous buffer with a pH range of 4 to 8.

17. The pharmaceutical composition of claim 1, wherein peak solubility of a DFX and the reference standard DFX after an 8 hr dissolution test in an aqueous buffer with a pH range of 4 to 8 have a ratio of greater than 4:1.

18. The pharmaceutical composition of claim 1, wherein in the AUC of the DFX in the composition and AUC of a reference standard DFX have a ratio that is greater than 4:3.

19. The pharmaceutical composition of claim 1, wherein said composition is formulated as an oral dosage form.

20. The pharmaceutical composition of claim 19, wherein the oral dosage form is a tablet, a capsule, or a sachet.

21. The pharmaceutical composition of claim 20, wherein the tablet is a round flat tablet, a round concave tablet, an elongated tablet, or a minitab.

22. The pharmaceutical composition of claim 20, wherein said oral dosage form is an extended release form, an immediate release form, a disintegrating tablet or an eroding tablet.

23. The pharmaceutical composition of claim 1, wherein the one or more pharmaceutically acceptable excipients comprises a lubricant.

24. The pharmaceutical composition of claim 23, wherein the lubricant is magnesium stearate.

* * * * *

UNITED STATES PATENT AND TRADEMARK OFFICE
CERTIFICATE OF CORRECTION

PATENT NO. : 10,265,301 B2
APPLICATION NO. : 15/185888
DATED : April 23, 2019
INVENTOR(S) : Dave A. Miller et al.

It is certified that error appears in the above-identified patent and that said Letters Patent is hereby corrected as shown below:

In the Claims

In Claim 4, Column 40, Lines 28-29, delete "poly(vinyl acetate)-co-polyvinylpyrrolidone) copolymer" and insert --poly(vinyl acetate)-co-poly(vinylpyrrolidone) copolymer-- therefor.

Signed and Sealed this
Twenty-fifth Day of June, 2019

Andrei Iancu
*Director of the United States Patent and Trademark Office*